(12) United States Patent
Weichert et al.

(10) Patent No.: US 7,700,075 B2
(45) Date of Patent: Apr. 20, 2010

(54) VIRTUAL COLONOSCOPY WITH RADIOLABELED PHOSPHOLIPID ETHER ANALOGS

(75) Inventors: Jamey P. Weichert, Fitchburg, WI (US); Marc Longino, Verona, WI (US)

(73) Assignee: Cellectar, LLC, Madison, WI (US)

( * ) Notice: Subject to any disclaimer, the term of this patent is extended or adjusted under 35 U.S.C. 154(b) by 1289 days.

(21) Appl. No.: 11/177,749

(22) Filed: Jul. 8, 2005

(65) Prior Publication Data

US 2006/0013767 A1 Jan. 19, 2006
US 2007/0098633 A2 May 3, 2007

Related U.S. Application Data

(60) Provisional application No. 60/521,831, filed on Jul. 8, 2004.

(51) Int. Cl.
A61B 5/055 (2006.01)
(52) U.S. Cl. ............... 424/9.3; 424/1.11; 424/1.65; 424/1.81; 424/1.85; 424/9.4; 424/9.1
(58) Field of Classification Search ............ 424/1.11, 424/1.37, 1.49, 1.65, 1.69, 1.73, 1.77, 1.81, 424/1.85, 1.89, 9.1, 9.2, 9.3, 9.32, 9.321, 424/9.322, 9.323, 9.34, 9.341, 9.35, 9.351, 424/9.36, 9.361, 9.362, 9.363, 9.364, 9.365, 424/9.37, 9.4, 9.42, 9.43, 9.45, 9.5, 9.6, 9.7, 424/9.8; 514/1, 75; 558/166
See application file for complete search history.

(56) References Cited

U.S. PATENT DOCUMENTS

| | | | |
|---|---|---|---|
| 4,925,649 A | 5/1990 | Counsell | |
| 4,965,391 A | 10/1990 | Counsell | |
| 5,087,721 A | 2/1992 | Counsell | |
| 5,347,030 A | 9/1994 | Counsell | |
| 5,369,097 A | 11/1994 | Salari | |
| 5,795,561 A | 8/1998 | Counsell | |
| 6,255,519 B1 * | 7/2001 | Counsell et al. | 558/166 |
| 6,417,384 B1 * | 7/2002 | Counsell et al. | 558/166 |
| 2002/0065429 A1 | 5/2002 | Counsell | |

OTHER PUBLICATIONS

Arthur, G. et al., The Inhibition of Cell Signaling Pathways . . . R. Biochim Biophys Acta. (1998) 1390:85-102.
Becher, R. et al., Phase II Trial of Orally Administered Miltefosine . . . Onkologie-Germany (1993) 16; 1:11-15.
Berdel, W.E. et al., Daily Oral Miltefosine (Hexadecylphosphocholine) . . . Onkologie-Germany (1992) 15:238-242.
Clezy, P.S. et al., The Chemistry of Pyrrolic Compounds, Aust. J.Chem., (1969) 22:239-49.
Counsell, R.E. et al., Tumor Visualization With a Radioiodinated Phospholipid . . . (1990) 31; 3:332-336.
Counsell, R.E. et al, Synthesis and Evluation of Radioiodinated Phospholipd Ether . . . Quart J. Nucl Med. (1997) 41(suppl 1):14-16.
Curley, SA et al., Radiofrequency Ablation of Unresectable Primary and Metastitic . . . Ann Surg. (1999) 230:1-8.
De Gramont, A. et al., Randomized Trial Comparing Monthly Low-Dose Leucovorin and . . . J. Clin. Oncol. (1997) 15:808-815.
Fong, Y. et al., Clinical Score for Predicting Recurrence After Hepatic Resection . . . Ann Surg. (1999) 230:309-318.
Giacchetti, S. et al., Phase III Multicenter Randomized Trial of Oxaliplatin Added . . . J. Clin. Oncol. (2000) 18:136-147.
Greven, K. et al., Can Positron Emission Tomography Distinguish Tumor . . . Cancer Journal Scientifica American (1997) 3:353-357.
Ike, H. et al., Results of Agressive Resection of Lung Matastases From Colorectal Carcinoma . . . Dis colon Rectum (2002) 45:468-473.
Imboden, M. et al., The Level of MHC Class I Expression on Murine Adenocarcinoma Can Change . . . Cancer Res. (2001) 61:1500-1507.
Kallman, R. F. Rodent Tumor Models in Experimental Cancer Therapy Pergamon Press, New York, (1987) pp. 111-132.
Lencioni, R. et al., Percutaneous Radiofrequency Thermal Ablation of Liver Malignancies: Techniques . . . Abdom Imaging (2001) 26:345-360.
Liebeskind L.S. et al., Heteroaromatic Thioether—Bornic Acid Cross-Coupling . . . Dept. of Chem., Emory University, Organic Letters (2002) 4; 6:979-981.
Longino, M.A. et al., Tumor Selective Rentention of NM404—Involvement of Phospholipase D. Molecular Imaging (2004), 3(3), (abstract).
Maier, O. et al., Fluorescent Lipid Probes: Some Properties and Application (A Review) Chemistry and Physics of Lipids 116 (2002) 3-18.
Mayr, N.A. et al., Method and Timing of Tumor Volume Measurement for Outcome . . . Int. J. of Rad., Oncol., Bio., Phys. (2002) 52; 1:14-22.
Meta-Analysis:Modulation of Fluorouracil by . . . Advanced Colorectal Cancer Meta-Analysis Project. J. clin. Oncol. (1992) 10:896-903.
Moser, A.R. et al., Specificity of NM404 for Hyperplasia Versus Neoplasia in the . . . Online Aug. 15-18, 2003 Presentation No. 305.

(Continued)

*Primary Examiner*—D L Jones
(74) *Attorney, Agent, or Firm*—Wood, Phillips, Katz, Clark & Mortimer

(57) ABSTRACT

The present invention provides agents and methods for dual modality virtual colonoscopy that gives both anatomical and functional information using hybrid CT/PET scanning. In preferred embodiments, the present invention provides radiolabeled tumor-specific agents and methods for distinguishing benign polyps from malignant tumors. In further embodiments, the present invention provides compositions and methods useful for distinguishing morphological and functional subregions of a selected region of tissue based on relative levels of phospholipid metabolism. Preferred radiolabeled tumor-specific agents are phospholipid ether analogs labeled with a halogen radioisotope. In certain preferred embodiments, the compositions including radiolabeled phospholipid ether analogs have therapeutic actions in addition to functionally identifying malignant tissue.

11 Claims, 19 Drawing Sheets

O'Dwyer, P.J. et al., Follow-Up of Stage B and C Colorectal Cancer in the United States and . . . Seminars in Onology (2001) 28:Suppl-9, pp. 45-49.

Penna, C., et al., Colorectal Metastasis (Liver and Lung), Surg. clin. North Amer. (2002) 82:1075-1090.

Pickhardt, P.J. et al., Computed Tomographic Virtual Colonoscopy to Screen for Colorectal . . . NE J. Med. (2003) 349; 23:2191-2200.

Plotzke, K.P. et. al., Selective Localization of a Radioiodinated Phospholipid Ether Analog in Human Tumor . . . J. Nucl. Med. (1993) 34(5):787-792.

Plotzke, K.P. et al., Selective Localization of Radioiodinated Alkylphosphocholine . . . Int. J. RadPart B, Nucl. Med. & Biology. (1992) 19(7):765-773.

Rampy, M.A. et al., Biological Disposition and Imaging of a Radioiodinated Alkylphosphocholine in Two Rodent . . . J. Nucl. Med. (1996) 37(9):1540-1545.

Rampy, M.A. et al., Synthesis and Biological Evaluation of Radioiodinated Phospholipid Ether Stereoisomers, J. Med. Chem. (1995) 38:3156-3162.

Saltz, L.B. et al., Irinotecan Plus Fluorouracil and Leucovorin for Metastiatic Colorectal Cancer . . . , N. Engl. J. Med. (2000) 343:905-91.

Snyder, F. et al., Alkyl and Alk-1-Enyl Ethers of Glycerol in Lipids From Normal and Neoplastic Human Tissues, Cancer Research. (1969) 29:251-257.

Snyder, F. et al., Occurrence and Nature of O-Alkyl and O-Alkyl-L-Enyl Moieties of Glycerol in Lipids of Morris . . . Biochem Biophys Acta. (1969) 176:502-510.

Solbiati, L. et al., Percutaneous Radio-Frequency Ablation of Hepatic Metastases From Colorectal Cancer: Long-Term . . . Radiology (2001) 221:159-166.

Stahl, A. et al., PET/CT Molecular Imaging in Abdominal Oncology, Abdominal Imaging (2004) 29:3(388-397).

Terwogt, J.M.M. et al., Phase II Trial of Topically Applied Miltefosine Solution in Optients With Skin-Metastasized . . . British J. of Cancer (1999) 79:1158-1161.

Wagner, R. et al., Boron-Dipyrromethene Dyes for Incorporation in Synthetic Multi-Pigment Light-Harvesting Arrays, Pure & Appl. Chem., (1996) 68; 7:1373-1380.

Weber, S.M. et al., Interleukin-1 Gene Transfer Results in CD8-Dependent Regression of Murine CT26 Liver Tumors, Ann. Surg. Oncol. (1999) 6:186-194.

Weichert, J.P. et al., Initial Clinical Imagining Results With NM404 in Non-Small Cell Lung Cancer, Molecular Imaging Online (2004) 3; 3:269-270.

Wichmann, M.W. et al., The Colorectal Cancer Study Group. Carcinoembryonic Antigen for the Detection . . . Anticancer Research (2000) 20:4953-4955.

Zasadny, K.R. et al., Predicted Dosimetry for I-131-NM404, A Phospholipid Ether Agent for Tumor Imaging and Possible Therapy, J Nucl Med. (1999) 40(5):39P.

Sik, M.D. et al., Neoplastic Transformation and Tumorrigensis Associated With Overexpress . . . Database Biosis(Online) (Oct. 2001) XP002365147 Database No. PREV200100523916, pp. 1641-1647.

Hirokazu O. et al., Increased Activity and Expression of Phospholipase D2 in Human . . . Database Biosis (Online) (2003) XP002365146 Database No. PREV00300566956, (abstract).

Dong-Young, N. et al., Overexpression of Phospholipase D1 in Human Breast Cancer Tissues, Database Biosis (Online) (Dec. 2000) XP002365186 Database No. PREV200100047408, (abstract).

Weichert, J. et al., Specificity of NM404 for Hyperplasia versus Neoplasia in the APC . . . Oasis—Online Abstrct Submission and Invitation System, 1996-2007, (abstract).

Weichert JP et al "Evaluation of 125I-NM404 in a Spontaneous Murine Pancreatic Adenocarcinoma . . .", Aug. 2003, 2nd Annual Meeting of the Society of Molecular Imaging, San, (abstract).

Weichert J. et al., Radioiodination Via Isotope Exchange in Pivalic Acid, Appl. Radiat Isot (1986) vol. 37, No. 8, 907-913.

Weichert J. et al., Polyiodinated Triglyceride Analogs As Potential Computed Tomography Imaging Agents for the Liver, J Med Chem (1995) 38, 636-646.

Pinchuk A et al., Synthesis and Structure-Activity Relationship Effects on the Tumor Avidity of Radioiodinated Phospholipid Ether Analogues, J Med Chem (2006), 49, 2155-2165.

\* cited by examiner

Extracellular    Membrane    Intracellular

Enzymes

PLE → Metabolized Product Cleared From Cell

Extracellular    Membrane    Intracellular

Enzymes?

PLE → Low / No Metabolism PLE Trapped in Membrane

FIG. 17A
FIG. 17B         FIG. 17C

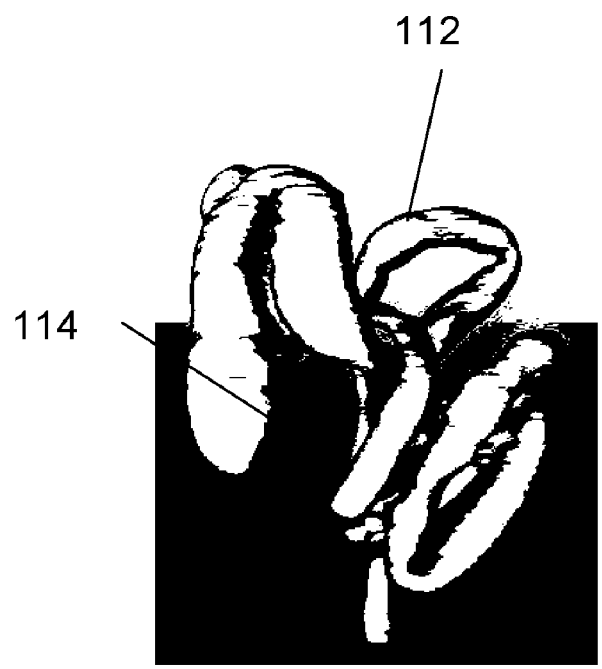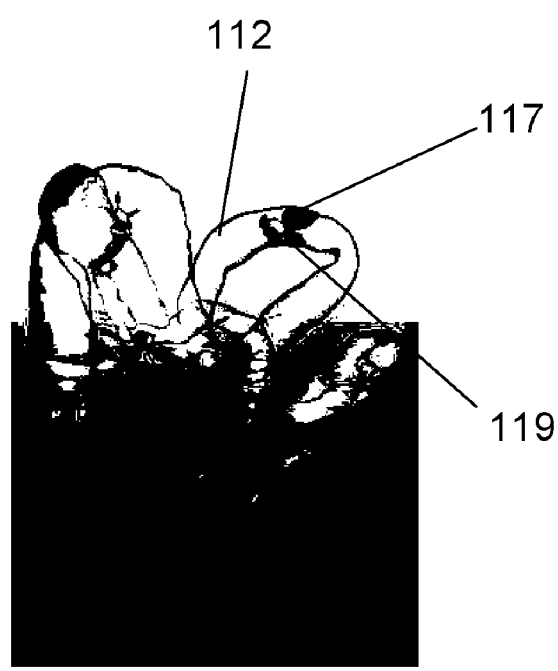
FIG. 21A      FIG. 21B
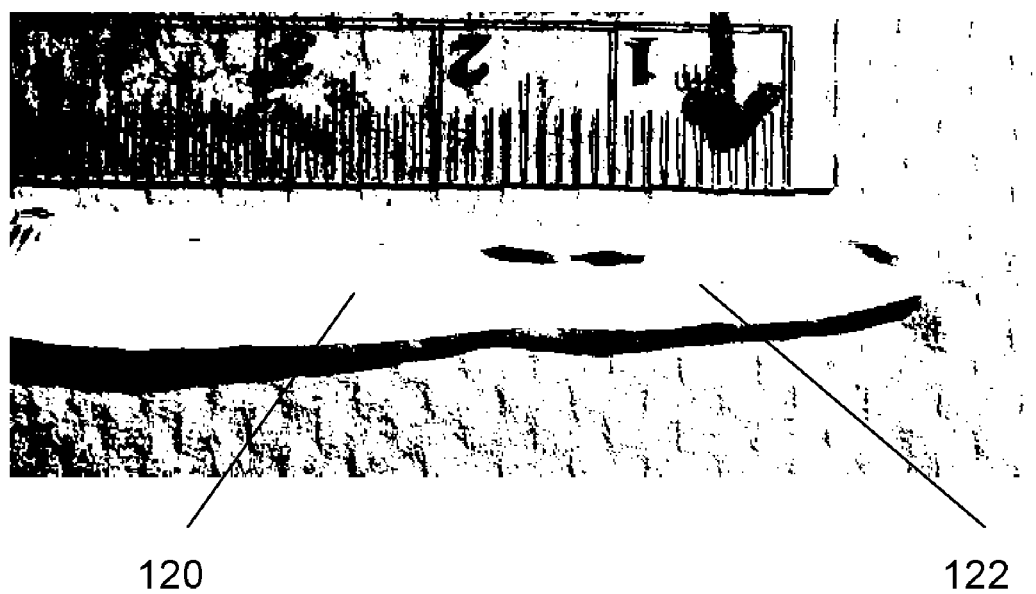
FIG. 22

VIRTUAL COLONOSCOPY WITH RADIOLABELED PHOSPHOLIPID ETHER ANALOGS

RELATED APPLICATIONS

This application claims benefit of U.S. Provisional Patent Application 60/521,831 filed Jul. 8, 2004, the entire contents of which are incorporated by reference for all purposes.

FIELD OF THE INVENTION

The invention generally relates to imaging of tumors and specifically relates to diagnostic imaging and characterization of tumors using virtual colonoscopy in combination with a radiolabeled tumor-specific agent, such as a phospholipid ether analog labeled with a radiohalogen.

BACKGROUND OF THE INVENTION

The early detection of cancer has been one of the primary goals of modern imaging technology, since the identification of a suspected tumor in a localized stage significantly improves the chances for successful treatment and elimination of the cancerous tissue. A large number of imaging strategies have therefore been designed, using a variety of techniques and modalities, to aid the physician in making an accurate diagnosis as early as possible.

Approximately 130,000 new cases of colorectal cancer are diagnosed each year in the United States. Thus colorectal cancer is the fourth most common cancer, accounting for 60,000 deaths per year (*Cancer Facts and Figures*. American Cancer Society 2001). Treatment depends primarily on the cancer stage, but may include surgery, radiation, chemotherapy, and/or radiofrequency or cryo-ablation. In routine follow-ups for colorectal cancer patients, however, determination of carcinoembryonic antigen (CEA), a colorectal tumor marker, and repeat colonoscopies (O'Dwyer P J, et al., Follow-up of stage B and C colorectal cancer in the United States and France. *Seminars in Oncology* 2001; 28: Suppl-9) fail to detect recurrent disease in over 50% of patients. See Wichmann M W, et al., The Colorectal Cancer Study Group; Carcinoembryonic antigen for the detection of recurrent disease following curative resection of colorectal cancer. *Anticancer Research* 2000; 20:4953-4955. Therefore, there is a need for development of additional methods for detection of recurrent disease.

Virtual colonoscopy, a non invasive scanning procedure performed by Computed tomography scanning in humans has been reported to be more accurate than traditional colonoscopy. (Pickhardt P J. et al., Computed tomographic virtual colonoscopy to screen for colorectal neoplasia in asymptomatic adults. *New England Journal of Medicine*. 349(23):2191-200, 2003 Dec. 4. Performed on a traditional multidetector helical CT scanner, virtual colonoscopy allows one to noninvasively scan the intestinal lumen anatomically for tumors but cannot characterize space occupying lesions as either polyps (adenomas) or adenocarcinomas (malignant). Determination of tumor type dramatically effects treatment planning and outcome for these patients.

In addition, functional information from CT scans is difficult to obtain during treatment and diagnosis using RF ablation and CT scanning. With contrast-enhanced helical CT, tumor vascularity may be assessed to some degree, but there is no way of accurately determining if viable tumor cells remain within the RF-ablated lesion. In addition, the thermal lesions created by RF normally have a rim of inflammation surrounding them on post procedure CT scans for up to 6 months post-ablation. PET scanning has been used to follow post-ablation patients, but the rim of inflammation surrounding RF thermal lesions normally displays increased uptake, even in the absence of a viable tumor. This decreases the sensitivity and specificity for early detection of recurrent tumor. Accordingly agents that are selective for and retained indefinitely by malignant tumor cells are preferable unlike fluorodeoxyglucose (FDG) which is not selective for tumor cells and is localized to infectious sites and hyperplasias (such as Barrett's Esophagus). Moreover compounds containing $^{124}$I, which has a 4 day physical half life and can thus be shipped anywhere in the world, are preferable to FDG, which has a 110 minute half life and therefore may only be have limited distribution within 200 miles of the production site.

Compounds that undergo prolonged retention (and are not metabolized) are preferable since it is more likely that they may have significant therapeutic potential when mated with an appropriate radioisotope like $^{125}$I, $^{131}$I or $^{211}$At. Also, compounds which can be labeled with a variety of iodine isotopes and have expanded versatility (diagnosis and therapy as well as a tool for experimental animal studies) are preferable to FDG, which is limited to $^{18}$F for PET scanning or potentially $^{19}$F (stable) for magnetic resonance imaging, albeit at very low sensitivity levels. Additional compounds disclosed to be useful for PET include $^{124}$I- or $^{131}$I-labeled 2'-fluoro-2'-deoxy-1-β-D-arabinofuranosyl-5-iodouracil (FIAU), $^{18}$F-labeled 9-[4-fluoro-3-(hydroxymethyl)butyl] guanine (FHBG), and $^{18}$F-labeled 9-[3-fluoro-1-hydroxy-2-propoxymethyl]guanine (FHPG). Regardless of its tumor targeting ability, $^{18}$F-FDG, due to its rapid metabolism in tumor cells, does not have potential for therapy. Therefore, other compounds are needed to investigate post therapeutic local recurrences.

Moreover, even where chemotherapy is the mode of treatment, improved monitoring of the response to chemotherapy is essential. Therefore, development of an early prognostic indicator to study response to chemotherapy to allow physicians to quickly discontinue use of ineffective chemotherapeutic regimens without exposing patients to the toxicity of prolonged treatments is desirable. Where External Beam Radiation Therapy is an alternate treatment for patients with tumors of similar histology, tumors may have dramatically different responses to curative-intent external radiation therapy (XRT). Some patients with rectal cancer treated with pre-operative radiation will have a complete response, while others with similar histology (at the light microscopy level) will have a poor response to treatment and will recur. Response to radiation is a predictive factor for ultimate tumor control and survival for many cancers, including many gastrointestinal cancers, lung cancer, head and neck cancer, and gynecologic cancers. Most response characterization methods, while very predictive of response, are performed after completion of treatment. While some intra-treatment clinical assessments are useful in adjusting treatment (Mayr, N. A., et al. Method and timing of tumor volume measurement for outcome prediction in cervical cancer using magnetic resonance imaging. *International Journal of Radiation Oncology, Biology, Physics* 2002; 52; 1:14-22), in most cases there is no accurate method of predicting tumor response during actual treatment. Such a test, especially one applicable to a broad range of tumor sites and histologies, would be very useful and desirable. Other treatment and diagnostic methods include molecular assays that have been proposed to predict response to therapy, and recent efforts include use of DNA microarrays to identify genetic changes that correlate with response or lack of response to treatment. These are investigational and none are in routine clinical use.

Yet other methods of diagnosis and treatment include use of imaging modalities to predict response during XRT treatment. Intra-treatment PET scans using FDG are under active investigation, wherein the isotope uptake in the primary tumor midway through radiation therapy is compared to the pre-treatment uptake. Several retrospective studies suggest patients with continued strong uptake during treatment have poorer tumor control outcomes than patients whose tumors are less FDG-avid during treatment (Greven, K., et al., Can positron emission tomography distinguish tumor recurrence from irradiation sequelae in patients treated for larynx cancer? *Cancer Journal Scientifica American* 1997; 3: 353-357). However, more effective screening, diagnostic and treatment agents and methods for various cancers are extremely desirable.

Unfortunately, conventional imaging techniques such as computerized tomography (CT) and MRI (magnetic resonance imaging) are limited in their ability to afford a conclusive diagnosis of a suspected lesion, since they are only capable of observing differences in the density or morphology of tissues. A more invasive and costly biopsy procedure is often necessary to provide a definitive diagnosis. In contrast, nuclear medicine techniques such as positron emission tomography (PET) and single photon emission tomography (SPECT) can provide functional or biochemical information about a particular organ or area of interest. However, the success of these nuclear imaging techniques depends in large part on the selective uptake and detection of appropriate radiopharmaceuticals. Selective uptake, in turn, depends upon the development of radiopharmaceuticals with a high degree of specificity for the target tissue. Unfortunately, the tumor-localizing agents developed thus far for oncological applications have had only limited application.

For example, one of these prior art compounds, $^{67}$Ga gallium citrate, was originally identified for its ability to accumulate in tumor tissue. Unfortunately, $^{67}$Ga gallium citrate is taken up by a variety of other non-tumor lesions as well, including inflammatory lesions, and unacceptable amounts of radioactivity can also accumulate in liver and spleen. The rapid buildup of a radiopharmaceutical in these organs can seriously interfere with the imaging of nearby lesions and also reduces the dosage that can safely be given to a patient.

An alternative approach has been to develop radiolabeled monoclonal antibodies (Mabs) directed to tumor-specific antigens. However, these monoclonal antibodies are specific only to the particular tumor tissue for which they have been produced, and therefore will not localize generally in neoplastic tissue. Moreover, the use of Mabs for diagnostic imaging has lead to additional problems, including varying degrees of antigen expression, low tumor uptake, non-specific binding and adverse immunogenic reactions and generally high liver localization.

In an attempt to address these problems, the present inventors have recently identified and developed a series of novel compounds demonstrating useful tumor selectivity. See, e.g., U.S. Pat. Nos. 4,925,649; 4,965,391; 5,087,721; 5,347,030; 6,255,519 and 6,417,384; all of which are herein incorporated by reference. It is believed that these radioiodinated phospholipid ether analogs take advantage of a unique biochemical characteristic of malignant tumor cells; i.e. the inability to metabolize phospholipid ether analogs relative to corresponding normal tissues. Although the precise mechanism of action is not fully understood, the prevailing hypothesis is that the phospholipid ether analogs become entrapped in malignant tumor cell membranes due to an apparent lack of appropriate metabolic enzyme. Accordingly, these compounds localize in tumor cells and become biochemically locked in place for diagnostic and/or therapeutic applications. Currently available oncologic PET agents such as $^{18}$F-FDG, localize in benign lesions and inflammatory sites as well as in tumors, and are thus not good indicators of malignancy.

Accordingly, there remains a significant need in the art for radiopharmaceuticals which exhibit a rapid clearance from non-target tissues as well as an extended half-life in the plasma, while still retaining its specificity and avidity for neoplastic tissue. Such an agent should not only assist in the non-invasive imaging and characterization of primary tumors and metastases, regardless of their location in the body, but should also serve as a carrier for a cytotoxic agent for site-specific eradication of malignant tumor tissue, especially as it relates to the most frequently diagnosed forms of cancer. It is further desirable that radiopharmaceuticals are selective for malignant tumors and not precancerous tissues including adenomas and hyperplasia.

Therefore, a readily available radiopharmaceutical that could accurately identify and potentially treat early metastatic disease in the patients with colorectal cancer would have an important impact on patient care, in terms of both staging and response to therapy. There remains a need for an accurate functional imaging technique based upon a tumor-specific function that can non-invasively screen the whole body using relatively inexpensive and widely available imaging devices.

SUMMARY OF THE INVENTION

In preferred embodiments, the present invention provides compositions and methods for dual modality virtual colonoscopy that give both anatomical and functional information using hybrid CT/PET scanning. In preferred embodiments, the present invention provides compositions including radiolabeled tumor-specific agents and methods for distinguishing benign polyps from malignant tumors. Preferred radiolabeled tumor-specific agents are phospholipid ether analogs labeled with a halogen radioisotope. For use in dual modality virtual colonoscopy using hybrid CT/PET scanning, the radioisotope should be a positron emitter. A particularly preferred radiolabeled tumor-specific agent is $^{124}$I-18-(4-iodophenyl)-octadecylphosphocholine ($^{124}$I-NM-404).

In certain embodiments, the present invention provides a method for distinguishing a benign structure from malignant tissue in a selected region of the digestive tract of a subject comprising the steps of providing a radiolabeled tumor-specific agent; administering the radiolabeled tumor-specific agent to the subject; using a first technique to visualize the morphology of a selected region having a benign structure and a malignant tissue; using a second technique to visualize the distribution in the selected region of radioactivity produced by the radiolabeled tumor-specific agent; and comparing the morphology of the selected region to the distribution of the radioactivity produced by the radiolabeled tumor-specific agent in the selected region thereby distinguishing a benign structure from malignant tissue.

The first technique can be computed tomography, magnetic resonance imaging, endoscopy or photography. The second technique can be positron emission tomography (PET), single photon emission tomography or scintigraphy.

Typically, the step of comparing the visualization of the morphology of the selected region to the visualization of the distribution of the radioactivity produced by the radiolabeled tumor-specific agent includes the step of producing an image of a three-dimensional structure by the reconstruction of two-dimensional images. In preferred embodiments, the step of comparing includes the step of superimposing the visualization of the distribution of the radioactivity produced by the radiolabeled tumor-specific agent on the visualization of the morphology of the selected region.

In particularly preferred embodiments, the radiolabeled tumor-specific agents have therapeutic functions as well as diagnostic functions. Preferably, the same administration of the radiolabeled tumor-specific agents produces both regression and shrinkage of the tumor as well as identification of the tumor. In certain embodiments, the same administration of the radiolabeled tumor-specific agents initially affords accurate detection, localization and characterization of the suspect mass, and when administered in combination with the same or different tumor-specific agent radiolabeled with a therapeutic isotope, also provides the ability to treat a malignant tumor. In other embodiments, the present invention provides agents and methods for monitoring the progress of therapy wherein the agent is avidly taken up by the tumor.

In preferred embodiments, the radiolabeled tumor-specific agent is a phospholipid ether analog labeled with a halogen radioisotope. In preferred embodiments, the phospholipid ether analog is covalently linked to a radioactive halogen. The radioactive halogen-substituent is suitably $^{18}$F, $^{36}$C, $^{75}$Br, $^{76}$Br, $^{77}$Br, $^{82}$Br, $^{123}$I, $^{124}$I, $^{125}$I, $^{131}$I and $^{211}$At of which $^{18}$F, $^{76}$Br, $^{123}$I, and $^{124}$I are preferable for diagnostic purposes while $^{77}$Br, $^{125}$I, $^{131}$I and $^{211}$At are preferable for therapeutic purposes. A preferred radioactive halogen-substituent for diagnostic purposes is $^{124}$I. In some preferred embodiments, a mixture of a phospholipid ether analog covalently linked to a radiohalogen selected from the group consisting of $^{18}$F, $^{76}$Br, $^{123}$I and $^{124}$I, can be administered mixed with a phospholipid ether analog covalently linked to a radiohalogen selected from the group consisting of $^{77}$Br, $^{125}$I, $^{131}$I and $^{211}$At. In certain preferred embodiments, a mixture of a phospholipid ether analog covalently linked to $^{124}$I, can be administered mixed with a phospholipid ether analog covalently linked to a radiohalogen suitable for therapeutic purposes. Suitable radiolabeled phospholipid ether analogs can be selected from the group consisting of $^{123}$I-18-(4-iodophenyl)-octadecyl phosphocholine, $^{124}$I-18-(4-iodophenyl)-octadecylphosphocholine, $^{125}$I-18-(4-iodophenyl)-octadecylphosphocholine, $^{131}$I-18-(4-iodophenyl)-octadecylphosphocholine and mixtures thereof. Suitable mixtures include a mixture of $^{124}$I-18-(4-iodophenyl)-octadecylphosphocholine and $^{123}$I-18-(4-iodophenyl)-octadecylphosphocholine, a mixture of $^{124}$I-18-(4-iodophenyl)-octadecylphosphocholine and $^{125}$I-18-(4-iodophenyl)-octadecylphosphocholine or a mixture of $^{124}$I-18-18-(4-iodophenyl)-octadecylphosphocholine and $^{131}$I-18-(4-iodophenyl)-octadecylphosphocholine.

In further preferred embodiments, the present invention provides a method for distinguishing a benign structure from malignant tissue in a selected region of the digestive tract of a subject comprising the steps of providing a tumor-specific phospholipid ether analog labeled with a halogen radioisotope; administering the phospholipid ether analog labeled with a halogen radioisotope to the subject; using computed tomography to visualize the morphology of a selected region having a benign structure and a malignant tissue; using positron emission tomography to visualize the distribution of the radioactivity produced by the radiolabeled tumor-specific agent; and comparing the morphology of the selected region to the distribution of the radioactivity produced by the radiolabeled tumor-specific agent thereby distinguishing a benign structure from malignant tissue.

In other embodiments, the present invention provides a method for monitoring the efficacy of treatment of colorectal cancer in a subject comprising the steps of determining the pre-treatment status of the colorectal cancer by the steps of providing a radiolabeled tumor-specific agent; administering the radiolabeled tumor-specific agent to the subject; using a first technique to produce a visualization of the morphology of a selected region having a benign structure and a malignant tissue; using a second technique to produce a visualization of the distribution of the radioactivity produced by the radiolabeled tumor-specific agent; and comparing the visualization of the morphology of the selected region to the visualization of the distribution of the radioactivity produced by the radiolabeled tumor-specific agent administering a selected treatment assessing the post-treatment status by the steps of providing a radiolabeled tumor-specific agent; administering the radiolabeled tumor-specific agent to the subject; using a first technique to produce a visualization of the morphology of a selected region having a benign structure and a malignant tissue; using a second technique to produce a visualization of the distribution of the radioactivity produced by the radiolabeled tumor-specific agent; and comparing the visualization of the morphology of the selected region to the visualization of the distribution of the radioactivity produced by the radiolabeled tumor-specific agent; and comparing the pre-treatment status to the post-treatment status to monitor the efficacy of the treatment.

In other embodiments, the present invention provides a method for distinguishing morphological and functional subregions of a selected region of tissue based on relative levels of phospholipid metabolism comprising the steps of providing a phospholipase substrate that is a radiohalogen-labeled phospholipid ether analog; selecting a region of a tissue suspected of having a plurality of morphologically distinct subregions of tissue further distinguished by different levels of phospholipid metabolism; contacting the region of the tissue with the radiohalogen-labeled phospholipid ether analog, wherein the radiohalogen-labeled phospholipid ether analog is taken up and selectively retained in the subregions of tissue having a relatively lower level of phospholipid metabolism; using a first technique to produce a representation of the morphology of the selected region; using a second technique to produce a representation of the distribution of the radioactivity produced by the selectively retained radiohalogen-labeled phospholipid ether analog; and comparing the representation of the morphology of the selected region to the representation of the distribution of the radioactivity produced by the selectively retained radiohalogen-labeled phospholipid ether analog, thereby distinguishing morphological and functional subregions of a selected region of tissue based on relative levels of phospholipid metabolism.

In other embodiments, the present invention provides a composition comprising a diagnostically effective amount of a radiolabeled phospholipid ether analog and a pharmaceutically acceptable carrier formulated for parenteral administration. The phospholipid ether analog can be suitably labeled with a halogen isotope selected from the group consisting of $^{18}$F, $^{36}$Cl, $^{75}$Br, $^{76}$Br, $^{77}$Br, $^{121}$Br, $^{123}$I, $^{124}$I, $^{125}$I, $^{131}$I, $^{211}$At and mixtures thereof. In preferred embodiments, the radiolabeled phospholipid ether analog is selected from the group consisting of $^{123}$I-18-(4-iodophenyl)-octadecylphosphocholine, $^{124}$I-18-(4-iodophenyl)-octadecylphosphocholine, $^{125}$I-18-(4-iodophenyl)-octadecylphosphocholine, $^{131}$I-18-(4-iodophenyl)-octadecylphosphocholine and mixtures thereof.

In yet other embodiments, the present invention provides a composition comprising a therapeutically effective amount of a radiolabeled phospholipid ether analog and a pharmaceutically acceptable carrier formulated for parenteral administration. The phospholipid ether analog can be suitably labeled with a halogen isotope selected from the group consisting of $^{18}F$, $^{36}Cl$, $^{75}Br$, $^{76}Br$, $^{77}Br$, $^{121}Br$, $^{123}I$, $^{124}I$, $^{125}I$, $^{131}I$, $^{211}At$ and mixtures thereof. In preferred embodiments, the radiolabeled phospholipid ether analog is selected from the group consisting of $^{123}I$-18-(4-iodophenyl)-octadecylphosphocholine, $^{124}I$-18-(4-iodophenyl)-octadecylphosphocholine, $^{125}I$-18-(4-iodophenyl)-octadecylphosphocholine, $^{131}I$-18-(4-iodophenyl)-octadecylphosphocholine and mixtures thereof.

In other embodiments, the present invention provides the use of a phospholipid ether analog for the manufacture of a radiopharmaceutical preparation for the identification of malignant tissue in a subject's digestive tract. In preferred embodiments, the present invention provides the use of a phospholipid ether analog for the manufacture of a radiopharmaceutical preparation for the detection or treatment of colorectal cancer. In further preferred embodiments, the present invention provides use of a phospholipid ether analog for the manufacture of a radiopharmaceutical preparation for dual modality virtual colonoscopy.

BRIEF DESCRIPTION OF THE DRAWINGS

FIG. 12A is a coronal microCT image (non-contrast-enhanced) is shown for anatomic comparison (T=tumor).

FIG. 14A is a low density surface rendering showing a large left axial mammary tumor. FIG. 14B is the high density surface rendering after blood pool CT contrast agent BP10 was administered to help locate tumor feeder vessels. FIG. 14C is a composite coronal CT image and high density surface rendering showing absolute feeder vessel localization. The orientation is from beneath in FIG. 14C, whereas FIG. 14A and FIG. 14B are viewed from above.

FIG. 17A-C show microCT images of a FVB×B6 Min mouse showing a large axillary mammary tumor. Coronal and axial slices are shown in FIG. 17A, whereas 3D-surface and coronal slices are displayed simultaneously in posterior (FIG. 17B) and anterior (FIG. 17C) views.

FIG. 21A and FIG. 21B are surface rendered (FIG. 21A) and transparent rendered (FIG. 21B) microCT images of the contrast-enhanced lower GI tract of an anesthetized mouse, showing the colon 112 and cecum 114 of the lower bowel. FIG. 21B also shows the distinction between a tumor 117 and a benign structure, a fecal pellet 119.

FIG. 22 is a photograph of an excised and dissected mouse colon 120 with a 3.5 mm diameter tumor 122.

FIG. 2C is 10 cm long.

DESCRIPTION OF THE PREFERRED EMBODIMENTS

Figure 1A:
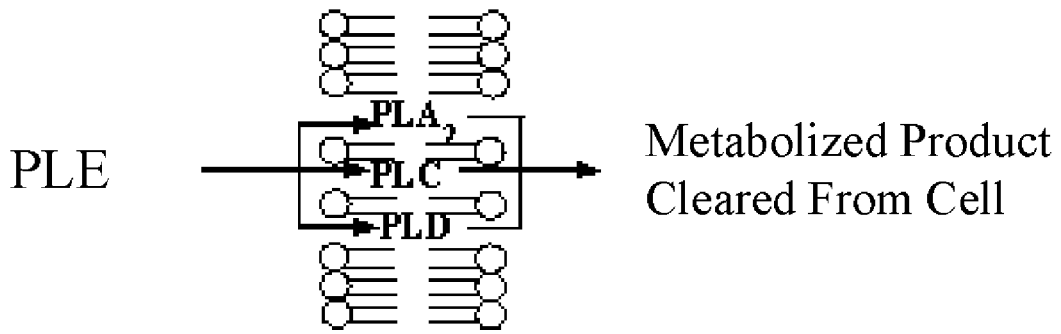
FIG. 1A and FIG. B are schematic diagrams of the different phospholipid metabolisms of benign and malignant cells with hypothetical differential effects on the uptake and tumor-specific retention of phospholipid ether analogs (PLE).

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to optical isomers and analogs, structural isomers and analogs, conformational isomers and analogs, and the like. In one embodiment, this invention encompasses the use of different optical isomers of a tumor-specific phospholipid ether analog of the present invention. It will be appreciated by those skilled in the art that the tumor-specific phospholipid ether analogs useful in the present invention may contain at least one chiral center. Accordingly, the compounds used in the methods of the present invention may exist in, and be isolated in, optically-active or racemic forms. Some compounds may also exhibit polymorphism.

It is to be understood that the present invention may encompass the use of any racemic, optically-active, polymorphic, or stereroisomeric form, or mixtures thereof, which form possesses properties useful in the treatment of tumor-related conditions described and claimed herein. In one embodiment, the tumor-specific phospholipid ether analogs may include pure (R)-isomers. In another embodiment, the tumor-specific phospholipid ether analogs may include pure (S)-isomers. In another embodiment, the compounds may include a mixture of the (R) and the (S) isomers. In another embodiment, the compounds may include a racemic mixture comprising both (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use. The terms "pharmaceutically acceptable salts" or "prodrugs" includes the salts and prodrugs of compounds that are, within the scope of sound medical judgment, suitable for use with subjects without undue toxicity, irritation, allergic response, and the like, commensurate with a reasonable benefit/risk ratio, and effective for their intended use, as well as the zwitterionic forms, where possible, of the compounds.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Compounds having N-oxides of amino groups, such as produced by reaction with hydrogen peroxide, are also encompassed.

"Pro-drug" means a pharmacologically inactive form of a compound which must be metabolized in vivo by a subject after administration into a pharmacologically active form of the compound in order to produce the desired pharmacological effect. After administration to the subject, the pharmacologically inactive form of the compound is converted in vivo under the influence of biological fluids or enzymes into a pharmacologically active form of the compound. Although metabolism occurs for many compounds primarily in the liver, almost all other tissues and organs, especially the lung, are able to carry out varying degrees of metabolism. For example, metabolism of the pro-drug may take place by hydrolysis in blood. Pro-drug forms of compounds may be utilized, for example, to improve bioavailability, mask unpleasant characteristics such as bitter taste, alter solubility for intravenous use, or to provide site-specific delivery of the compound. Reference to a compound herein includes pro-drug forms of a compound.

A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. For example, if a compound contains a carboxylic acid functional group, a pro-drug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound comprises an alcohol functional group, a pro-drug can be formed by the replacement of the hydrogen atom of the alcohol group with a group such as $(C_1-C_6)$alkanoyloxymethyl, 1-$(C_1-C_6)$alkanoyloxy)ethyl, 1-methyl-1-$(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and alpha-aminoacyl, or alpha-aminoacyl-alpha-aminoacyl, where each alpha-aminoacyl group is independently selected from the naturally occurring L-amino acids, P(O)$(OH)_2$, —P(O)(O$(C_1-C_6)$alkyl$)_2$ or glycosyl (the radical resulting from the removal of a hydroxyl group of the hemiacetal form of a carbohydrate).

If a compound comprises an amine functional group, a pro-drug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural alpha-aminoacyl or natural alpha-aminoacyl-, —C(OH)C(O)OY wherein Y is H, $(C_1-C_6)$alkyl or benzyl, —C(OY$_1$)Y$_1$ wherein Y$_0$ is $(C_1-C_4)$ alkyl and Y$_1$ is (($C_1-C_6$)alkyl, carboxy($C_1-C_6$)alkyl, amino($C_1-C_4$)alkyl or mono-N- or di-N,N—$(C_1-C_6)$alkylaminoalkyl, —C(Y$_2$) Y$_3$ wherein Y$_2$ is H or methyl and Y$_3$ is mono-N- or di-N,N—$(C_1-C_6)$-alkylamino, morpholino, piperidin-1-yl or pyrrolidin-1-yl.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes method utilizing derivatives of the tumor-specific phospholipid ether analogs. The term "derivatives" includes but is not limited to ether derivatives, acid derivatives, amide derivatives, ester derivatives and the like. In addition, this invention further includes methods utilizing hydrates of the tumor-specific phospholipid ether analogs. The term "hydrate" includes but is not limited to hemihydrate, monohydrate, dihydrate, trihydrate and the like.

This invention further includes methods of utilizing metabolites of the tumor-specific phospholipid ether analogs. The term "metabolite" means any substance produced from another substance by metabolism or a metabolic process.

As defined herein, "contacting" means that the tumor-specific phospholipid ether analog used in the present invention is introduced to a sample containing cells or tissue in a test tube, flask, tissue culture, chip, array, plate, microplate, capillary, or the like, and incubated at a temperature and time sufficient to permit binding of the tumor-specific phospholipid ether analog to a receptor or intercalation into a membrane. Methods for contacting the samples with the tumor-specific phospholipid ether analog or other specific binding components are known to those skilled in the art and may be selected depending on the type of assay protocol to be run. Incubation methods are also standard and are known to those skilled in the art.

In another embodiment, the term "contacting" means that the tumor-specific phospholipid ether analog used in the present invention is introduced into a subject receiving treatment, and the compound is allowed to come in contact in vivo. In further embodiment, the term "contacting" means that the tumor-specific phospholipid ether analog used in the present invention is introduced into a subject requiring screening for tumors, and the compound is allowed to come in contact in vivo.

A "pharmaceutically acceptable" ester or salt as used herein means an ester or salt form of the active ingredient which is compatible with any other ingredients of the pharmaceutical composition and which is not deleterious to the subject to which the composition is to be administered. The terms "pharmaceutically acceptable salts" or "prodrugs" includes the salts and prodrugs of compounds that are, within the scope of sound medical judgment, suitable for use with subjects without undue toxicity, irritation, allergic response, and the like, commensurate with a reasonable benefit/risk ratio, and effective for their intended use, as well as the zwitterionic forms, where possible, of the compounds.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

A "diagnostically effective amount" means an amount of a compound that, when administered to a subject for screening for tumors, is sufficient to provide a detectable distinction between a benign structure and a malignant tumor. The "diagnostically effective amount" will vary depending on the compound, the condition to be detected, the severity or the condition, the age and relative health of the subject, the route and form of administration, the judgment of the attending medical or veterinary practitioner, and other factors.

For purposes of the present invention, "treating" or "treatment" describes the management and care of a subject for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

The form in which the active compound is administered to the cell is not critical; the active compound need only reach the cell, directly or indirectly. The invention encompasses preparation and use of medicaments and pharmaceutical compositions comprising a compound described herein as an active ingredient.

A compound of the present invention is administered to a subject in a diagnostically or therapeutically effective amount. A compound of the present invention can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A compound of the present invention can be administered using an immediate release formulation, a controlled release formulation, or combinations thereof The term "controlled release" includes sustained release, delayed release, and combinations thereof In preferred embodiments, a phospholipid ether analog of the present invention is combined with a pharmaceutically acceptable carrier to produce a pharmaceutical preparation for parenteral administration.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with a tumor-specific phospholipid ether analog according to the present invention. As used herein, administration can be accomplished in vitro, i.e. in a test tube, or in vivo, i.e. in cells or tissues of living organisms, for example, humans.

In certain embodiments, the present invention encompasses administering the compounds useful in the present invention to a non-human or human subject. "Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "pharmaceutical composition" means therapeutically effective amounts of the tumor-specific phospholipid ether analog together with suitable diluents, preservatives, solubilizers, emulsifiers, and adjuvants, collectively "pharmaceutically-acceptable carriers." As used herein, the terms "effective amount", "diagnostically effective amount" and "therapeutically effective amount" refer to the quantity of active agent sufficient to yield a desired effect without undue adverse side effects such as toxicity, irritation, or allergic response. The specific "effective amount" will, obviously, vary with such factors as the particular condition being diagnosed or treated, the physical condition of the subject, the species of the subject, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of disease (e.g., colorectal cancer); and (b) the reversal or stabilization of such disease. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20™, Tween 80™, Pluronic F68™, bile acid salts), solubilizing agents (e.g., glycerol, polyethylene glycerol), anti-oxidants (e.g., ascorbic acid, sodium metabisulfite), preservatives (e.g., Thimerosal™, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, tansdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1 M and preferably 0.05 M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the tumor-specific phospholipid ether analog alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the tumor-specific phospholipid ether analog can be administered to a patient by, for example, subcutaneous implantation of a pellet. In a further embodiment, a pellet provides for controlled release of tumor-specific phospholipid ether analog over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administerable by the invention can be prepared by known dissolving, mixing, granulating, or tablet-forming processes. For oral administration, the tumor-specific phospholipid ether analogs or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the tumor-specific phospholipid ether analogs or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. Active therapeutic ingredients are often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the tumor-specific phospholipid ether analogs or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

Generally, NM404 is a promising new tumor-selective diagnostic imaging agent to monitor the treatment response of several tumor treatment modalities. Radioiodinated NM404, a second-generation phospholipid ether analog, had displayed remarkable tumor selectivity in 10/10 xenograft tumor models and more recently in another 17/17 spontaneous rodent tumor models. Due to a lack of metabolic phospholipase enzymes in the membranes of tumor cells, the prevailing hypothesis of this approach is that phospholipid ether analogs become trapped exclusively in tumor cell membranes because of their inability to become metabolized and eliminated. Thus, the differential clearance rates of phospholipid ethers from normal cells versus viable tumor cells form the basis of this concept. Results obtained in a variety tumor models indicate that NM404 is sequestered and selectively retained by viable malignant tumor cells and localizes in both primary and metastatic lesions regardless of anatomic location including those found in lymph nodes. Unlike FDG, this agent does not localize in infectious sites. Other advantages of NM404 over FDG include the following: NM404 is selective for and retained indefinitely by malignant tumor cells whereas FDG in not selective for tumor cells and goes to infectious sites and hyperplasias (Barrett's Esophagus). Further, since $^{124}$I has a 4 day physical half life it can be shipped anywhere in the world whereas FDG with its 110 min half life, may have limited distribution within 200 miles of the production site. NM404 undergoes prolonged retention (not metabolized) and therefore affords a significant therapeutic potential when mated with an appropriate radioisotope like $^{131}$I or $^{125}$I whereas FDG does not possess any therapeutic potential. NM404 can be labeled with a variety of iodine isotopes expanding it's versatility (diagnosis and therapy as well as a tool for experimental animal studies) whereas FDG is limited to $^{18}$F for PET scanning or potentially $^{19}$F (stable) for magnetic resonance imaging albeit at very low sensitivity levels. Regardless of its tumor targeting ability, due to its rapid metabolism in tumor cells, it has no potential for therapy. NM404 affords the potential to not only accurately predict local tumor response to various treatment modalities, but also allows detection of distant metastatic lesions in cases of sub-therapeutic primary tumor treatment.

Specifically for dual modality virtual colonoscopy, NM404 or one of its phospholipid ether (PLE) analogs, affords the potential to allow non invasive detection and characterization of intestinal lesions when used independently via PET or SPECT imaging) or in combination with CT based virtual colonoscopy when performed on a hybrid CT/PET scanner. Moreover, if malignancy is confirmed by uptake of NM404 or its PLE analog into the intestinal lesion, it could be used subsequently as a therapeutic agent when labeled with a therapeutic radio-halogen. As a third use, NM404 could be used to monitor tumor response in patients with colon or intestinal cancer following conventional therapeutic paradigms. Since it is only taken up and selectively retained by malignant tumor cells, it would be administered following conventional treatment and integrity of tumor cells would be evaluated noninvasively by PET or PET-CT imaging. Localization at the original tumor site would imply remaining functional tumor cells, whereas, lack of radioactivity from the original tumor site would imply successful treatment. It may also be helpful in traditional colonoscopy if the colonoscope is equipped with an appropriate radiation detector.

NM404 is selective for malignant cells (27/27 types thus far), unlike FDG, which is known to also localize in hyperplastic cells and inflammatory sites. We have shown that phospholipid ether analogs like NM404 and its predecessor NM324, do not localized in inflammatory lesions in the rat Carageenan assay. NM404 undergoes selective retention in malignant cells and because it can be labeled with any halogen including all iodine isotopes including those with therapeutic emissions ($^{125}$I, $^{131}$I, as well as the halogen astatine-211 which is also a halogen with very iodine-like chemical properties) therefore has much therapeutic potential, unlike FDG.

NM404 does not cross the intact blood brain barrier and therefore is much better than FDG in brain tumor detection than FDG which of course localizes quite well in normal brain tissue thus limiting its use in brain tumor detection.

NM404 labeled with iodine-124 can be made in one location and shipped anywhere in the world, unlike $^{18}$F-FDG, which due to its 110 minute physical half-life, has a limited delivery radius and thus requires many production sites.

Relative to other oncologic PET agents labeled with iodine-124, like [124]I-FIAU, NM404 iodine is much more stable to in vivo deiodination due to its aromatic C—I bond structure. Many of the others, including FIAU, which contain aliphatic iodine, are known to deiodinate rapidly following injection.

While FDG permits scanning 45 minutes after injection a longer wait with NM404 improves contrast due to progressive concentration in tumors. In clinical practice, since NM404 is specific for malignant tumors, then an imaging delay time of up to 24 or 48 hours is not a problem. For tumors it is possible to scan within 6 hours due to tomographic nature of PET.

NM404 has demonstrated remarkable specificity for neoplastic tissue but not for pre-neoplastic tissue in many experimental tumor models. The high tumor to background avidity and tumor selectivity of NM404 suggests it can be potentially superior to $^{18}$F-FDG PET scanning for intra-treatment tumor imaging. The precise mechanism of tumor specificity of NM404 is under investigation, and currently is not as well described as the glucose utilization mechanism for $^{18}$F-FDG uptake. It is not well established whether NM404 uptake and selective retention in neoplastic tissue depends on the viability of that tissue, or if this uptake phenomenon is related to some membrane or matrix component that is independent of tissue viability. If this uptake and specificity are linked to tumor viability, it would follow that NM404 uptake in tumors recently sterilized by radiation would be non existent or poor, whereas tumors resistant to radiation would show continued uptake. Recently, the inventors demonstrated NM404 uptake and killing in both radio-sensitive and radio-resistant squamous cancer cells (SCC1 and SSC6) in nude mice. Such an assay is useful in managing patients treated with radiation therapy since patients manifesting no post-treatment NM404 localization would indicate successful treatment, whereas those with resistant tumors (continued uptake of NM404) could be offered other non-radiation options (surgery, chemotherapy, etc).

One approach to the development of sensitive, more available imaging exams is to design carrier molecules which are capable of selectively delivering a radiopharmaceutical probe to the desired target tissue. The inventors' approach has been to capitalize on unique biochemical or pharmacological properties of molecules displaying a high degree of tissue or tumor selectivity.

Snyder and coworkers observed that a variety of animal and human tumor cells contain much higher concentrations of naturally occurring ether lipids in the cell membranes than normal tissue. See Snyder F, Wood R. Alkyl and alk-1-enyl ethers of glycerol in lipids from normal and neoplastic human tissues. *Cancer Research*. 1969; 29:251-257: Snyder F, Blank M L, Morris H P. Occurrence and nature of o-alkyl and o-alkyl-1-enyl moieties of glycerol in lipids of Morris transplanted hepatomas and normal rat livers. *Biochem Biophys Acta*. 1969; 176:502-510. These authors proposed that the accumulation of ether lipids in tumors was a result of a lower capacity of tumor cells to metabolize these lipids due to a lack of key metabolic enzymes. The inventors have capitalized on this observation by synthesizing a number of radioiodinated phospholipid ether (PLE) analogs as potential tumor-selective imaging agents. Several of these PLE analogs have exhibited a striking and apparently universal ability to localize in and be selectively retained by a wide variety of spontaneous and transplanted rat, murine, and human tumor models (25/25).

Figure 1B:
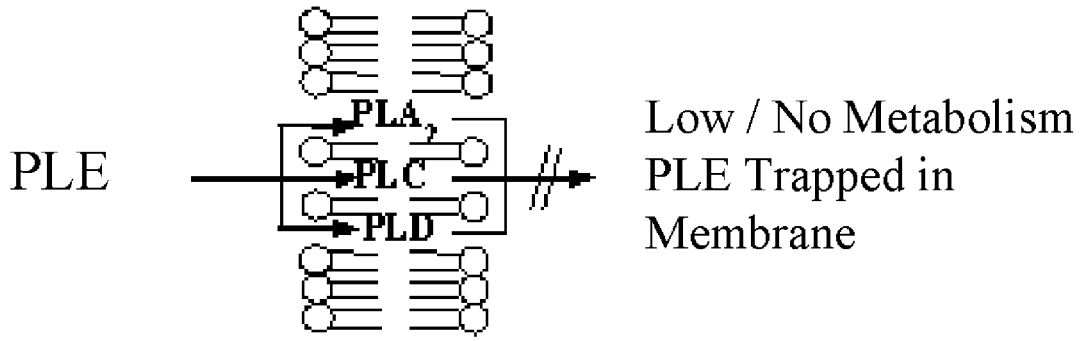

The working hypothesis (FIG. 1) is that phospholipid ethers become trapped in viable tumor cell membranes because of their inability to become metabolized and eliminated. This hypothesis is supported by experimental results of studies of enzyme activity and expression reported below. Typical metabolic enzymes include phospholipase $A_2$, ($PLA_2$), phospholipase C, (PLC) and phospholipase D, (PLD). Extraction of tumors following administration of radioiodinated phospholipid ether agents showed the presence of only the intact agent, whereas analysis of the urine and feces revealed only metabolites. While not being bound to a specific hypothesis or mechanism of action, these results, and those described below, indicate that it is the differential clearance rates of phospholipid ethers from normal cells versus tumor cells as well as underlying differences in cellular phospholipid metabolism, form the basis of the tumor-specificity of the phospholipid ether analogs of the present invention.

Preliminary results obtained in over 25 xenograft and spontaneous tumor models (Table 1) have shown NM404 to undergo selective uptake and prolonged retention in all of the tumors tested. Because the agent is metabolized to some extent in the liver, the inventors avoided earlier compound evaluation in liver tumor models due to high liver background radioactivity levels. Further, because NM404 affords lower liver background levels than its predecessors, the inventors expanded evaluation into liver tumors in light of the fact that imaging patients with HCC has been problematic. Many patients have underlying cirrhosis and therefore it is difficult to distinguish regenerating nodules from HCC on cross sectional imaging. Moreover, preliminary studies evaluating PET scanning with FDG have shown only 20-50% sensitivity in detecting the disease. Verhoef C., et al., Liver (2002) 22:51-56. Further, PET FDG is not useful in diagnostic screening in brain. Similarly FDG has not useful in evaluating disease in liver due to high natural uptake by hepatocytes Following examples describe various aspects of the present invention. These examples are described for illustrative purposes only and should not be deemed to narrow or limit the scope of the present invention.

Example 1

Synthesis, Radiolabeling, and Formulation of NM404

The synthetic approach was based on the copper-catalyzed cross-coupling reaction of Grignard reagents with alkyl tosylates or halides for the alkyl chain elongation (see the scheme below). The synthesis was started from p-iodobenzyl alcohol 1 which was converted into p-iodobenzyl bromide 2 by reaction with trimethylsilyl bromide. p-Iodobenzyl bromide 2 was further coupled with Grignard reagent 3 in the presence of $Li_2CuCl_4$ as a catalyst. 12-(p-Iodophenyl)dodecanol 5 obtained after deprotection of the first coupling product 4 was converted into tosylate 6. In the next step, tosylate 6 was coupled with Grignard reagent 7 containing 6 carbon atoms and this completed the chain elongation process. TUP deprotection of 8 gave 18-(p-iodophenyl)octadecanol 9 which was converted into 10 (NM404) by two-step procedure as shown in the scheme.

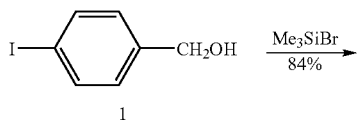

1

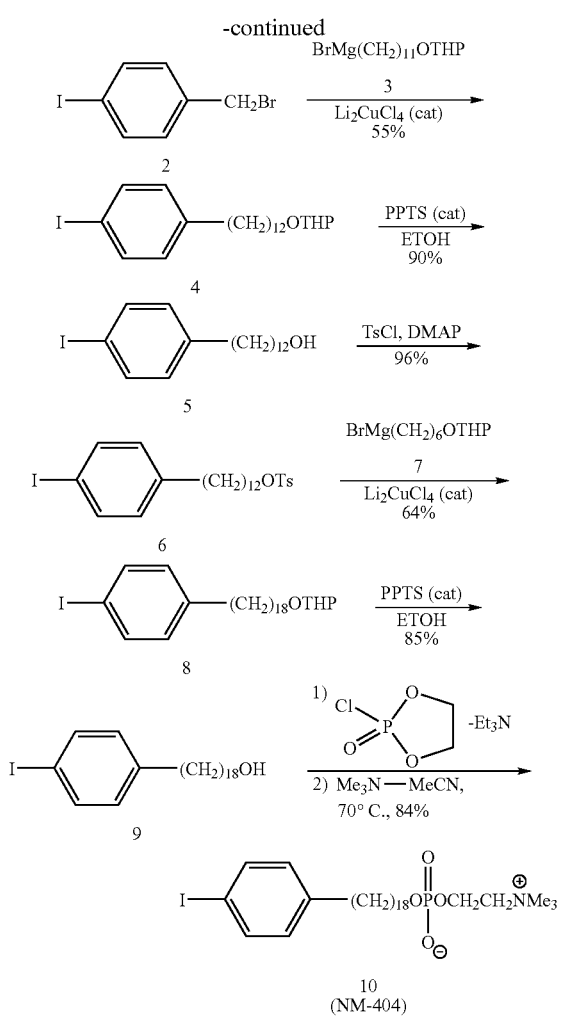

Further, rapid high yield synthesis process for labeling NM404 with any isotope if iodine, including $^{124}I$, $^{125}I$ and $^{131}I$ was carried out by the following process:

First, an aluminum heating block apparatus was preheated to 145° C. and a condenser was prepared using a 5 ml disposable syringe barrel fitted with a bent 1.5 inch 18 ga disposable needle and a rubber septum at the top.

Second, the HPLC system was initiated and the reservoir was filled with filtered degassed solvent (hexane/isopropanol/water (40:52:8). The system was equilibrated followed by a systematic check-up of the ancillary systems such as the pump, detectors, chart recorders and computer integrators.

Third, a 3-ml disposable syringe charcoal trap as prepared by using a glass wool plug in bottom, filling the syringe with 2.5 mL with granulated charcoal, adding another glass wool plug and inserting a septum on top. A short tubing adaptor needle was placed on the syringe and an 18-ga needle was inserted through the septum on the top. The charcoal trap was connected to the top of the condenser and vented to the atmosphere through a sodium thiosulfate trap.

Fourth, 5 mg of ammonium sulfate was added in 20 μl of deionized water in 2 ml borosilicate glass v-vial followed by 20 μg of unlabeled NM404 in 20-μl of absolute ethanol to the vial. The vial was gently swirled or flicked to ensure mixing and 6 borosilicate glass beads (3 mm) was also added to the vial. The vial was then sealed with a Teflon-coated butyl rubber septum and an aluminum crimp cap. The septum was punctured with an 18-ga needle and the desired amount of aqueous sodium iodide-131 (in 0.1 N NaOH, typically 5 mCi in 15 μl) was added via a Hamilton microsyringe through the septum. The vial was again gently swirled or flicked to ensure mixing. The vial was assayed in a dose calibrator.

Fifth, the charcoal trap syringe was inserted into the reaction vial and the reaction vial was lowered into the heating block well (filled half way with sand). The reaction vial was heated at 145° C. for 40 min during which most of the solvent distilled off and condensed in the condenser. A stream of air (4×25 ml) was slowly inserted through the reaction vial with a 25-ml syringe. The temperature of the reaction vile was increased to 155° C. and heating was continued for an additional 30 minutes. The reaction vial was removed from the block heater and the condenser/trap assembly was disconnected and discarded and vial was allowed to cool to room temperature.

Sixth, 0.5 ml of absolute ethanol was added into the reaction vial. The vial was gently swirled and assayed in the dose calibrator.

Seventh, a radio-TLC analysis of the crude labeled product mixture was conducted on silica gel (chloroform/methanol/water (65/35/4).

Eighth, Amberlite IRA 400 resin column was prepared by presoaking 1.0 g of resin in 5 ml of abs. ethanol for 30 minutes. Ethanol was decanted and the resin was rinsed with two additional 5 ml portions of ethanol. The wet resin was added into a 3 ml disposable syringe barrel with a glass wool plug at the bottom and fitted with an Acrodisc filter and a 2 way stopcock. The ethanolic solution of the crude radioiodinated product was gradually eluted through the resin column into a 5 ml vial.

Ninth, a septum was inserted and the solvent was blown off with a stream of nitrogen. A charcoal syringe was attached on the outlet of the vial prior to initiating nitrogen flow. Once dry, 50 μl of ethanol was used to dilute and transfer contents to a 300 μl v-vial. The source vial was rinsed with a second 50 μl ethanol wash and transferred to the v-vial.

Tenth, HPLC pump was stabilized and a solvent flow of 1.0 ml/min was established. The reaction mixture was purified by HPLC on a Perkin-Elmer cartridge silica column (4.3×33 mm, 3 μm silica) eluted with hexane/isopropanol/water (40:52:8) at 1.0 ml/min. Peak detection was performed by UV at 230 and 254 nm and by radioactivity. Once the appropriate peak was collected in a sterile vial, a small sample for radio-TLC analysis was removed and the remaining solvent was evaporated with a stream of nitrogen to give the desired compound as a dry residue. Specific activity was calculated as necessary.

Eleventh, Polysorbate-20™ was added at a ratio of 0.1 μl/1.0 μg of NM404 to the flask from a stock solution of 5% Polysorbate 20™ in absolute ethanol. Polysorbate 20™ is the pharmaceutical grade of Tween 20™ that is now used in both human and animal studies with NM404. The solvent was removed by rotary evaporation for 10 min at <30° C. The residue was dissolved with mixing in sufficient sterile water to yield a 2% Polysorbate-20 solution. The formulated product was passed through a sterile 0.2 μm Pall-Gelman Acrodisc filter (13 mm) into a dry, sterile, multidose vial (Hollister-Stier) vented with another sterile 0.2 μm filter. 100 μl of product solution was diverted into a vial for QC analysis.

Twelfth, radioactivity was measured in the dose calibrator and quality control tests (sterility, apyrogenicity) were performed.

All unlabeled NM404 were taken from the original stock batch that recently underwent acute toxicology testing in order to minimize potential synthetic differences between studies. Radioiodination of NM404 was routinely achieved by an isotope exchange reaction in a melt of pivalic acid developed by the inventors (Weichert J P, Van Dort M E, Groziak M P, Counsell R E. Radioiodination via isotope exchange in pivalic acid. *Int J Appl Rad Isotopes.* 1986; 37:907-913) or by the new method described herein and prepared for injection according to standard methods described by the inventors (Rampy M A, Brown R S, Pinchuk A N, Weichert J P, Skinner R W, Fisher S J, Wahl R L, Gross M D, Ethier S P, Counsell R E. Biological disposition and imaging of a radioiodinated alkylphosphocholine in two rodent models of breast cancer. J Nucl Med. 1996; 37(9): 1540-1545). This procedure was used effectively for preparing sterile material for the initial human trials with NM324, the predecessor of NM404 and has been used over 40 times to prepare $^{125}$I- and $^{131}$I-labeled NM404. Generally, following purification and accurate mass quantification by HPLC, the radio-pharmaceutical was dissolved in absolute ethanol (50-500 μl) and Polysorbate-20™ (0.1 μl/μg of compound). The ethanol is removed under vacuum and the residue dissolved in sterile water to give a final solution containing no more than 2-3% Polysorbate-20. Sterilization was achieved by filtration through a sterile 0.2 μm filter unit. Final radiochemical purity must exceed 97% before using in a subject. Quantification and calculation of final specific activity were achieved by HPLC analysis using known mass standards, and quantification of radioactivity ($^{125}$I) was accomplished by dilution and counting in a P E Wallac gamma-counter in order to avoid attenuation concerns. Quantification of higher energy isotopes including $^{131}$I were done with a dose calibrator with built in settings for these isotopes. Specific activities of 1 mCi per 100 μg of radioiodinated NM404 were typically achieved. Injection volumes were typically around 100 μl per mouse. Tissue distribution data were expressed as a percent injected dose (±SEM) per gram of tissue and also as percent injected dose per organ when whole organs were weighed according to published procedures (Rampy M A, Brown R S, Pinchuk A N, Weichert J P, Skinner R W, Fisher S J, Wahl R L, Gross M D, Ethier S P, Counsell R E. Biological disposition and imaging of a radioiodinated alkylphosphocholine in two rodent models of breast cancer. *J Nucl Med.* 1996; 37(9):1540-1545). At each time point, tumor-to-tissue-ratios were calculated on a percent injected dose per gram of tissue basis.

General tissue distribution (TD) analysis: Biodistribution studies were performed in female mice according to the standard procedure developed by the inventors (Weichert J P, et al., Polyiodinated Triglyceride Analogs as Potential CT Imaging Agents for the Liver. *J Med Chem* 1995; 38:636-646). Radioiodinated NM404 (5 μCi in 100 μl) was administered via tail vein injection. At the predetermined time points animals (3 per time point) were euthanized by exsanguination while under pentobarbital anesthesia. A total of 16 tissues including blood, plasma, adrenal glands, bladder, bone marrow, fat, heart, kidney, liver, lung, muscle, spleen, ovaries, skin, thyroid, and tumor were excised, rinsed, and dissected free of extraneous tissue. Large organs were minced and duplicate tissue samples was weighed and placed in plastic tubes for isotope counting. Injection site and residual carcass radioactivity were also determined in a well counter. These standard procedures have been utilized for many years in the inventors' laboratory under appropriate animal care and radiation safety approval. Tissue distribution tables were generated by a computer program which produces decay-corrected tissue radioactivity concentration data on a percent injected dose/g, % kg dose, and percent injected dose/organ ±SEM basis. At each time point, tumor to tissue ratios were calculated based on a percent injected dose per gram of tissue basis. A control TD study (3 mice/time point, 15 total mice) were performed on tumor bearing mice at 4, 7, 14, 21, and 28 days most NM404 injection in order to establish comparative TD tables for all of the therapeutic regimens.

General imaging protocols: Animals received $^{125}$I-NM 404 (10 μCi) via tail vein injection and at predetermined time-points thereafter were anesthetized (sodium pentobarbital anesthesia, 0.06 mg/g bw) and underwent radionuclide scanning using a Bioscan AR2000 radio-TLC scanner modified for mouse imaging (2 mm high resolution collimator/1 min acquisition time per lane/1 mm lane increments). Data were quantitated and presented using Winscan 2D software from Bioscan. Once excised, control and treated tumors were also scanned ex vivo on the Bioscan unit in order to allow for more accurate region-of-interest (ROI) analysis by eliminating whole body radionuclide attenuation. Animals (sodium pentobarbital anesthesia, 0.06 mg/g bw) underwent microCT scanning (Imtek MicroCAT I, 390 step acquisition/43Kvp/410 μA; CTI Molecular Imaging, Inc., Knoxville, Tenn.) using medium resolution acquisition parameters. Data sets were reconstructed 3-dimensionally and are visualized with AMIRA 3D-visualization software. The software allows for ROI density analysis and convenient on-screen measuring.

Example 2

High Specific Activity Synthesis and Radiolabeling

In the synthesis of high specific activity NM-404, cold NM-404 is first coupled with bis-(neopentyl glycolato)diboron in the presence of Pd catalyst to form arylboronate ester. In the second step, the arylboronate ester is subjected to radioiodo-deboronation using radioactive sodium iodide and chloramine-T to obtain radioiodinated NM-404 with high specific activity.

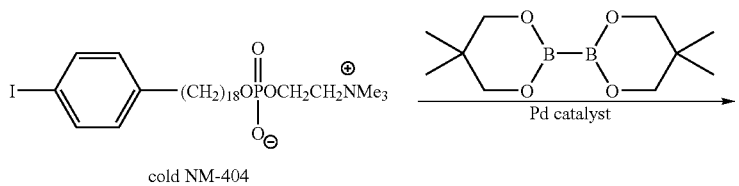

cold NM-404

-continued

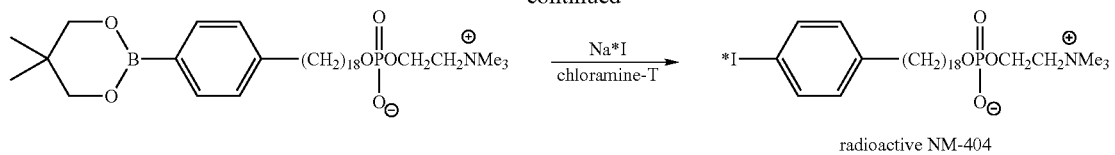

radioactive NM-404

Other esters of glycol esters of diboronic acid can also be used in the first reaction, for example: bis-(pinacolato)diboron and bis-(hexylene glycolato)diboron.

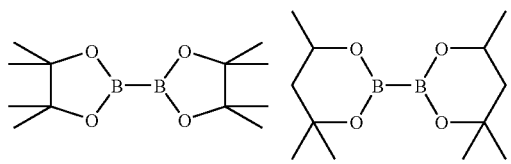

The important criterion of the high specific activity synthesis is that the final labeled compound, for example, $^{131}$I-NM404 and its precursor, the boronate compound must be easily separable by HPLC. This ensures that literally every molecule of NM404 that is isolated by HPLC is radiolabeled. Theoretical specific activity of the compound is about 2500 curies/mmol. The existing isotope exchange method is limited to about 10 curies/mmol specific activity. For therapy, this is important since the likely amount of compound required for the treatment of a subject, for example with the radioisotope $^{131}$I-NM404, is about 60-100 mCi. This new high specific activity synthesis will provide much larger mass dose of radiolabeled NM404 as compared to the currently available isotope exchange conditions, especially required to attain a therapy dose of $^{131}$I analog.

Example 3

Preclinical Studies with PLE Analogs

Phospholipid ethers can easily be labeled with iodine radioisotopes using an isotope exchange method described above. The iodophenyl phospholipid ether analogs are specifically designed so that the radioiodine affixed to each molecule is stable to facile in vivo deiodination. Over 20 radiolabeled PLE compounds were synthesized and tested in vitro and in vivo. Two of these, namely NM294 and NM324 [12-(3-iodophenyl)-dodecyl-phosphocholine], initially showed the most promise in animal tumor localization studies. These prototype compounds, labeled with $^{125}$I, selectively localized in tumors over time in the following animal tumor models; 1) Sprague-Dawley rat bearing Walker 256 carcinosarcoma; 2) Lewis rat bearing mammary tumor; 3) Copenhagen rat bearing Dunning R3327 prostate tumors; 4) Rabbits bearing Vx2 tumors; and 5) athymic mice-bearing human breast(HT39), small cell lung (NCI-69), colorectal (LS174T), ovarian (HTB77IP3), and melanoma tumors. Optimal tumor localization of these agents takes from one to several days.

Mechanistic Studies with PLE Analogs: NM324 and NM404 are similar in structure to miltefosine (hexadecylphosphocholine), an antitumor ether lipid studied most extensively in Europe. The antitumor properties of miltefosine and several other antitumor phospholipid ether analogs have been demonstrated in a wide range of tumor cell lines including prostate-, bladder-, and terato-carcinomas, murine and human leukemias, as well as lung, colon, ovarian, brain and breast cancers (Arthur G. Bittman R. The inhibition of cell signaling pathways by antitumor ether lipids. *Biochim Biophys Acta.* 1998; 1390:85-102). In contrast to many anticancer drugs, these phospholipid ether analogs do not bind directly to DNA and are not mutagenic. Although the precise antiproliferative mechanism of action has not been determined, they apparently act at several tumor cell sites. These compounds have been associated with a variety of cellular effects including transport, promotion of cytokine formation, apoptosis induction, and interference with a variety of key lipid metabolism and cell signaling enzymes most of which are located in the cellular membrane. Although a debate exists regarding the mode of uptake into cells, the majority of reports now support the idea that these ether lipids are directly absorbed into cell membranes where they accumulate. A widespread belief is that these agents act by perturbing membrane phospholipid metabolism; however, cellular distribution studies with these agents have been limited by spontaneous cellular compartmental redistribution during homogenization and subcellular fractionation procedures. In contrast to the tracer imaging doses (several μg) the inventors have employed, antitumor effects are seen only at doses generally exceeding 300-1000 mg per day (Arthur & Bittman, 1998).

Figure 15:
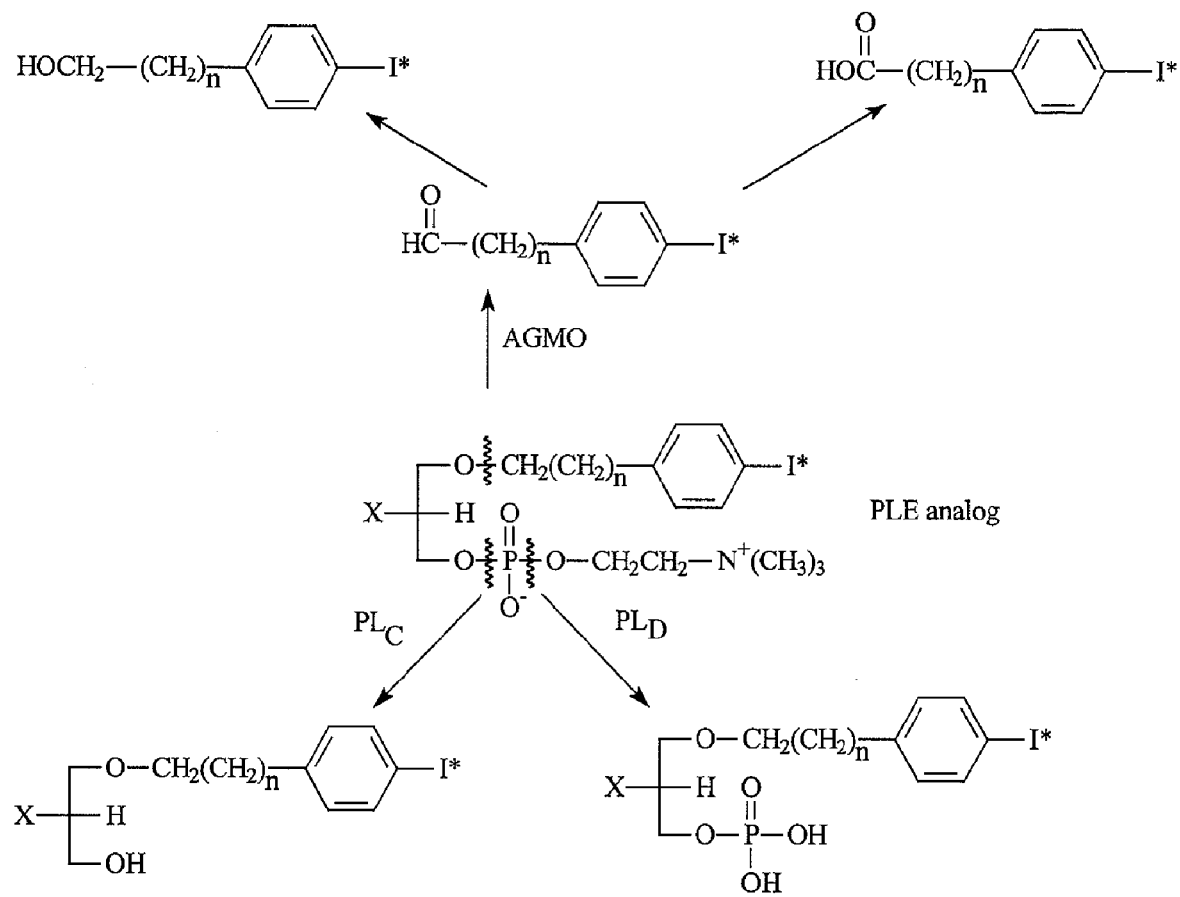
FIG. 15 is a schematic diagram of pathways of the enzymatic metabolism of phospholipid ethers.

Formal metabolism studies were conducted on several PLE analogs including NM324, the predecessor of NM404. In these studies, each agent was examined to determine their ability to serve as substrates for enzymes associated with PLE metabolism. As shown in FIG. 15, three major enzymatic pathways are involved in the metabolism of PLE. O-Alkyl glycerol monooxygenase (AGMO) is responsible for cleavage of the alkyl ether linkage at C-1 to form either the long chain fatty alcohol or fatty acid. Phospholipases C (PLC) and D (PLD), on the other hand, give rise to the glycerol or phosphatidic acid products, respectively. Using a microsomal AGMO enzyme preparation, NM324 was not a substrate for this enzyme when compared to [$^3$H]-lyso-PAF (platelet activating factor), which was extensively metabolized. In a similar fashion, NM324 was analyzed as a substrate for PLD isolated from *Bacillus cereus* and was not hydrolyzed relative to 1-palmitoyl-2-[3H]-palmitoyl-L-3-phosphatidylcholine (DPPC), which underwent significant hydrolysis.

Finally, several PLE analogs were subjected to a PLD assay. The PLD, which was isolated from cabbage, is similar to mammalian PLD in that the cabbage form affords phosphatidylethanol-type products in addition to phosphatidic acid when the enzymatic reaction is performed in the presence of ethanol. Several of the PLE analogs subjected to these assay conditions did give rise to the phosphatidylethanol product indicating possible interaction with PLD Several NM404 precursors were also subjected to in vitro metabolism studies in various cell lines including Walker 256 tumor cells, rat muscle (H9c2), and rat hepatocytes. In these studies, the extent of metabolism was determined on the basis of radiolabeled products formed after incubation for various time periods and the results normalized to cell number or the amount of cellular protein. Subsequent lipid extraction of the incubation medium and cell suspension demonstrated little generation of PLE metabolites in the Walker tumor cells whereas a significant production of metabolites was seen in both the muscle cells and hepatocytes over the 48 h time period studied. These results correlate nicely with in vivo biodistribution studies completed on all analogs. Although several studies have been completed, the role of metabolic trapping in the uptake and retention of radiolabeled PLE analogs in tumor cells is not well defined and currently remains an active area of examination.

Figure 2:
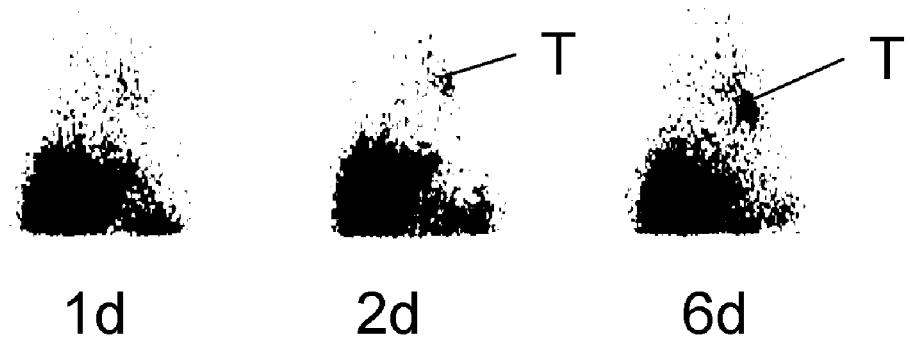
FIG. 2 provides scintigraphic images of the anterior chest of Patient 03 acquired at 1, 2, and 6 days after IV administration of 1 mCi $^{131}I$-NM324. Uptake is seen in the left lingular lung cancer (T) with increasing tumor-to-background ratios over time.

Clinical Evaluation of NM324: Of several promising first generation PLE analogs, NM324 was easier to chemically synthesize and was thus selected as the lead compound for initial clinical studies. Although images obtained in five human lung cancer patients detected tumors, images were complicated by high liver radioactivity (FIG. 2).

Figure 3A:
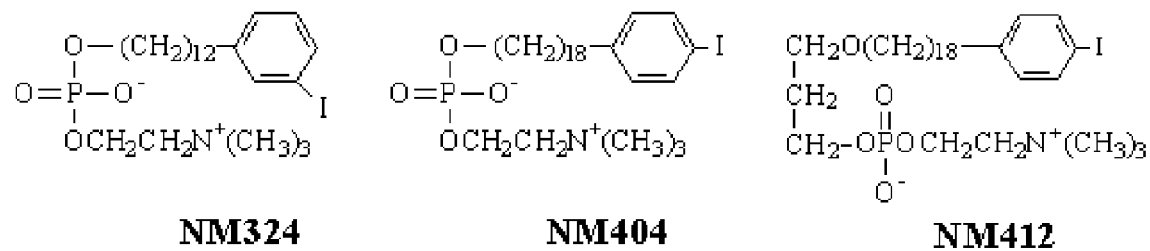
FIG. 3A and FIG. 3B provide the chemical structures of three iodinated phospholipid ether analogs designated as NM324 (FIG. 3A), NM404 (FIG. 3A and FIG. 3B) and NM412 (FIG. 3A).
Figure 3B:
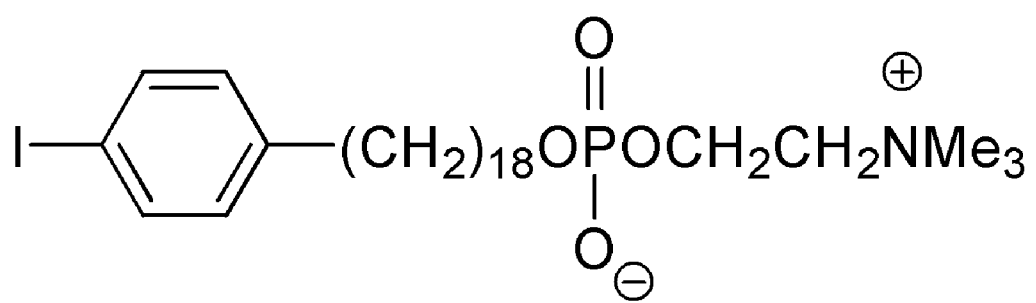

Second Generation PLE Analogs: In order to decrease liver uptake and prolong the plasma phase, nine structural analogs of NM324 were synthesized and radiolabeled with $^{125}$I for initial image analysis in Copenhagen rats bearing Dunning R3327 prostate tumors. Based upon this initial screen, NM347, NM404 [18-(4-iodophenyl)-octadecylphosphocholine] and NM412 (FIG. 3) were selected to undergo further imaging and biodistribution analysis in animal-tumor models.

More recent imaging studies with NM404 and NM412 in animal models showed that both were superior to NM324 in visualizing a variety of tumors. Significantly, lymph node metastases were clearly delineated in a metastatic prostate tumor model following intravenous administration of either NM404 or NM412. Most importantly, the tracer was not retained by uninvolved lymph nodes. (FIG. 4A).

Figure 4A:
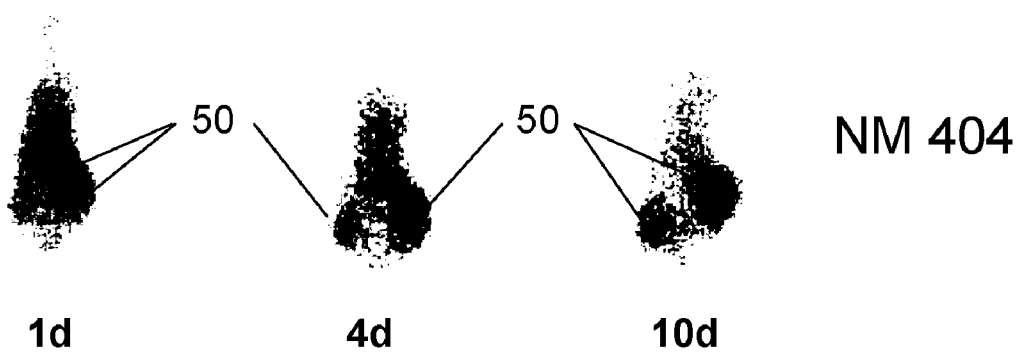
FIG. 4A and FIG. 4B illustrate the results of a scintigraphic comparison of the distribution of phospholipid ether analogs NM404 (FIG. 4A) and NM324 (FIG. 4B) in a SCID mouse tumor model following IV administration of the radiolabeled phospholipid ether analogs. Note in that most of the NM324 (FIG. 4B) activity is found in the gut 55 and not in the tumor 50 (implanted in the thigh) whereas NM404 (FIG. 4A) correctly identified a tumor 50 in both the left and the right thighs. With time the radiolabeled phospholipid ether analog NM 404 becomes more selectively localized in the tumor 50 compared to the rest of the tissue, which was not observed for the radiolabeled phospholipid ether analog NM 324.
Figure 4B:
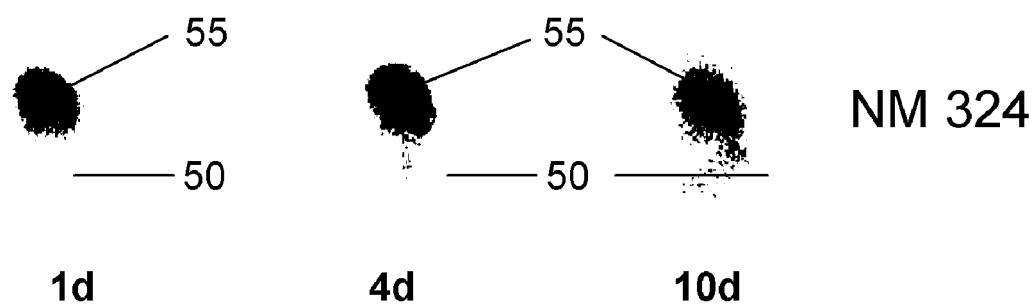
Figure 4C:
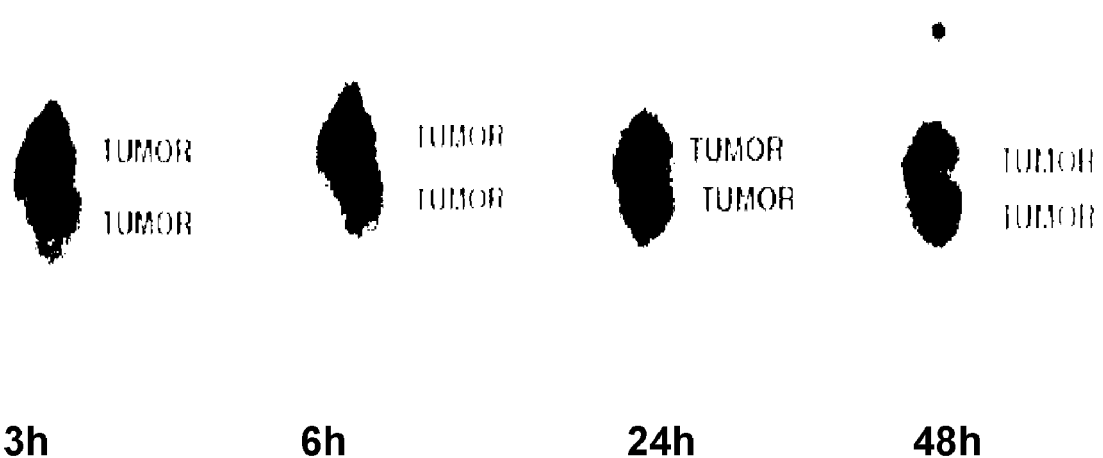
FIG. 4C shows scintigraphic images following IV administration of the radiolabeled phospholipid ether analog NM404 showing localization of the phospholipid ether analog in Dunning R3327 metastatic prostate tumors ("tumor") in a Copenhagen rat with primary tumor site (leg) surgically removed. Two lymph node tumors were verified post mortem.

FIG. 4A and FIG. 4B illustrate the results of a scintigraphic comparison of the distribution of phospholipid ether analogs NM404 (FIG. 4A) and NM324 (FIG. 4B) in a SCID mouse tumor model following IV administration of the radiolabeled phospholipid ether analogs. Note in that most of the NM324 (FIG. 4B) activity is found in the gut 55 and not in the tumor 50 (implanted in the thigh) whereas NM404 (FIG. 4A) correctly identified a tumor 50 in both the left and the right thighs. With time the radiolabeled phospholipid ether analog NM 404 becomes more selectively localized in the tumor 50 compared to the rest of the tissue, which was not observed for the radiolabeled phospholipid ether analog NM 324. FIG. 4C shows scintigraphic images following IV administration of the radiolabeled phospholipid ether analog NM404 showing localization of the phospholipid ether analog in Dunning R3327 metastatic prostate tumors ("tumor") in a Copenhagen rat with primary tumor site (leg) surgically removed. Two lymph node tumors were verified post mortem.

Although conducted in a prostate model, this finding is particularly relevant to breast cancer wherein lymph node involvement is such an important prognostic indicator. A preliminary pilot study conducted in SCID mice bearing human A549 NSCLC tumors were encouraging and demonstrated that NM404 overcomes the problem of high first pass clearance of NM324 by the liver. NM404 shows excellent tumor visualization, especially striking in the delayed images, with minimal liver and kidney uptake in comparison with NM324 (cf FIG. 4A and FIG. 4B). Tissue biodistribution studies further confirmed the high levels of radioactivity residing in the tumors. Although imaging results were similar with NM404 and NM412, dosimetry data obtained in rats revealed lower kidney doses were found with NM404 relative to NM412, and thus NM404 was selected for further studies. Comparative biodistribution data for NM324 and NM404 in SCID mice with prostate and A549 lung cancer tumor models have revealed high tumor to normal tissue ratios and tumor uptake exceeding 25% of the injected dose with NM404.

Animal imaging studies performed in mouse models aimed at determining the uptake characteristics in a wide variety of tumor models are summarized in Table 1. Preliminary results in B6 Apc$^{Min}$/+ mice indicate that NM404 is not taken up by adenomatous polyps but is taken up and retained by mammary adenocarcinomas in this model, thus indicating a possible specificity for malignant tumor cells. These studies are aimed at determining the potential of NM404 to noninvasively characterize tumors. NM404 has displayed significant tumor uptake and retention in every adenocarcinoma model studied.

Figure 5:
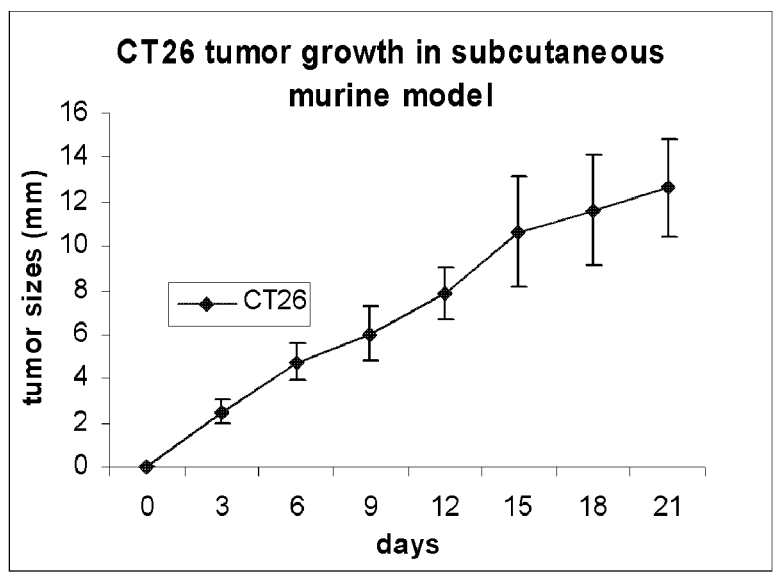
FIG. 5 is a graphical representation of the growth of tumors in mice that had received a subcutaneous injection of CT-26 cells.

Relevance of CT-26 Murine Tumor Model: Inventors explored NM404 as a predictor of tumor response in a murine (BALB/C mice) model with subcutaneous CT-26 cell inoculation into the flanks of the mice. The CT-26 cell line is a poorly differentiated murine adenocarcinoma that was induced by rectal injection of N-nitroso-N-methylurethane in Balb/c mice. The cell line is simple to grow in vitro and results in a predictable growth pattern when injected in the vasculature (tail vein injection, metastatic model), into the skin (FIG. 5) or liver. FIG. 5 is a graphical representation of the growth of tumors in mice that had received a subcutaneous injection of CT-26 cells. See Weber, S M, Shi F. et al., Interleukin-12 gene transfer results in CD8-dependent regression of murine CT26 liver tumors. *Ann Surg Oncol* 1999; 6:186-194; Imboden M, et al., The level of MHC class I expression on murine adenocarcinoma can change the antitumor effector mechanism of immunocytokine therapy. *Cancer Res* 2001; 61:1500-1507. Because the cell line is derived from a colorectal cancer, this murine model is highly clinically relevant for these studies.

Imaging Results with NM404 in CT-26 Tumors: This study shows that a radiohalogen labeled phospholipid ether analog, NM404, is localized in subcutaneous CT-26 xenografts. Two mice were injected (IV tail vein) with $^{125}$I-NM404 (10 μCi) and subsequently imaged on a modified Bioscan AR-2000 TLC Imaging Scanner to acquire 2 dimensional scintigraphic images of radioisotope distribution (Bioscan, Washington, D.C.; equipped with high resolution 1 mm collimator and 2-D image acquisition and analysis software) at 1, 4, and 7 days post injection. On day 7, the animal was euthanized and the tumor removed, photographed, and scanned ex vivo on the Bioscan (FIG. 6). Ex vivo scanning is standard protocol in the inventors' lab due to the severe tissue attenuation effects associated with iodine-125. Each animal also underwent microCT scanning (FIG. 7) on day 7 prior to euthanasia and dissection of the tumor.

Figures 6A, 6B, 6C:
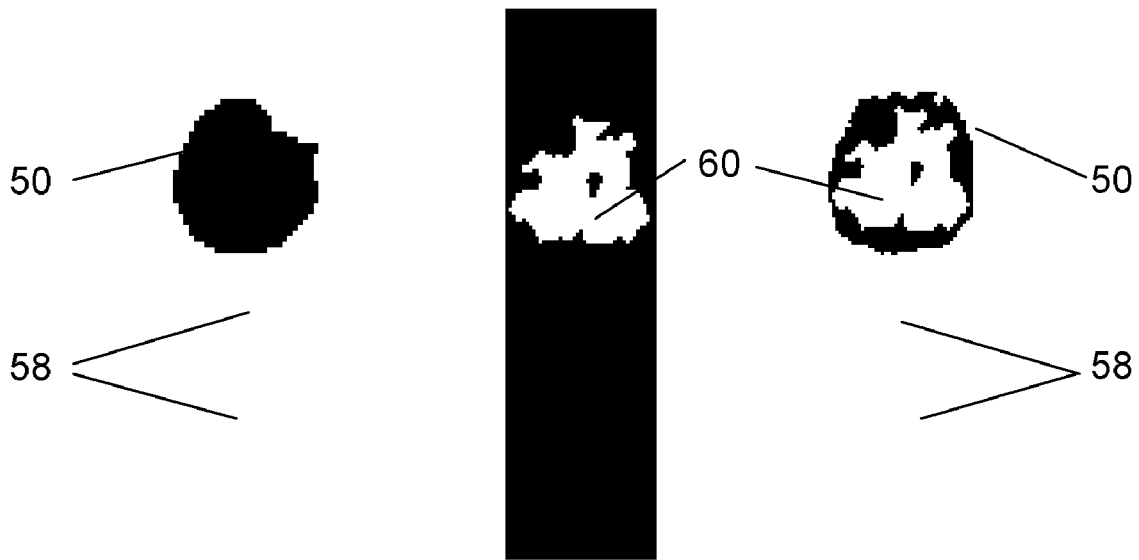
FIG. 6A is a photographic image of an excised CT-26 tumor 50 and excised left and right lymph nodes
FIG. 6B is a scintigraphic image of the excised tumor and lymph nodes of FIG. 6A, showing significant radioactivity 60 localized to the tumor and little or no radioactivity localized to the lymph nodes.
FIG. 6C is a image produced by fusing of the digital photographic image of FIG. 6A and the digital scintigraphic image of FIG. 6B, showing the correlation of radioactivity and the tumor.
Figure 7A:
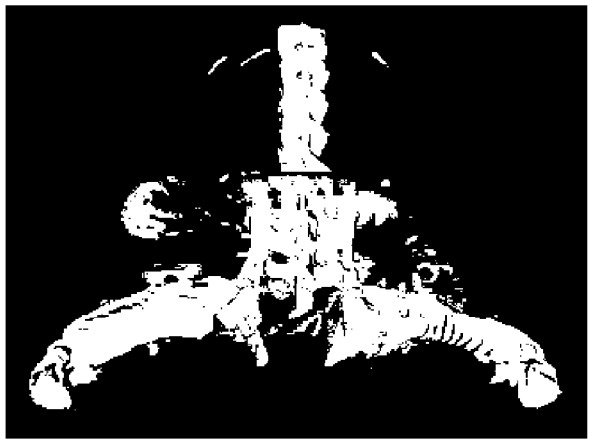
FIG. 7A-FIG. 7D show microCT images of the live mouse of FIG. 6 showing the size and location of the CT-26 tumor (arrows). 3D-surface rendered and planar slice images are shown in FIG. 7A & FIG. 7B while coronal and axial slices (90 μm thickness) are shown in FIG. 7C & FIG. 7D, respectively.
Figure 7B:
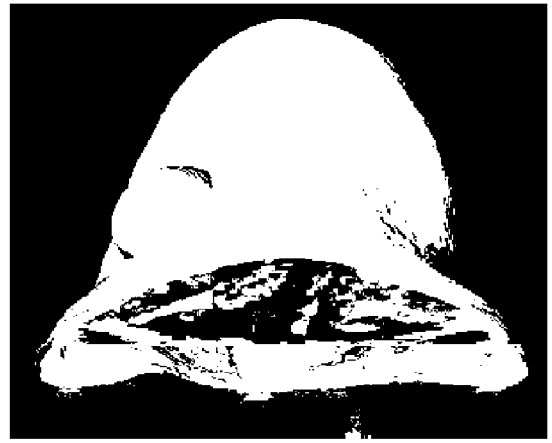
Figure 7C:
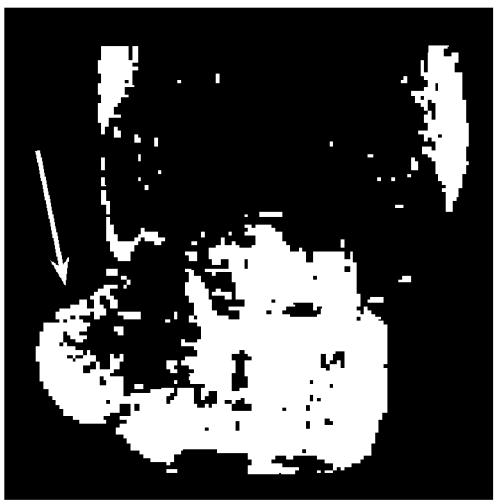
Figure 7D:
Figures 8A, 8B:
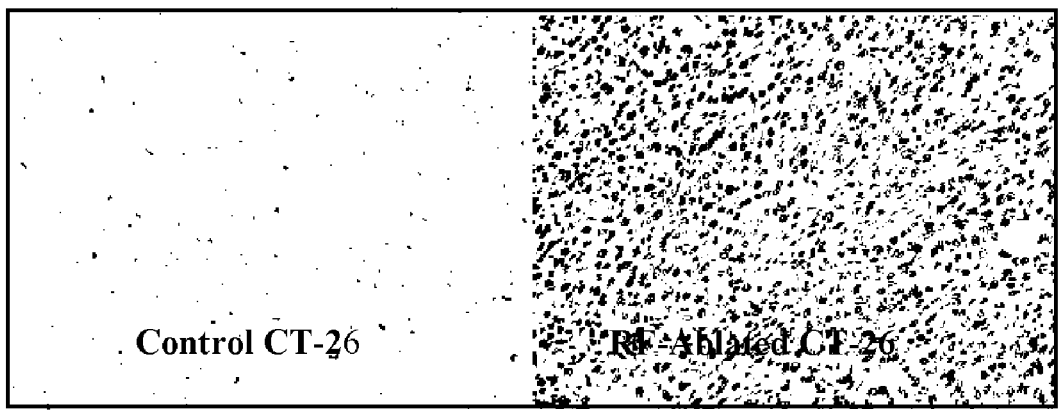
FIG. 8 shows photographic images of histologic sections (H&E) of normal (FIG. 8A) and RF-ablated (FIG. 8B) CT-26 tumor. The cells in the ablated section have lost membrane integrity and appear pyknotic.

Focal hot spots of radioactivity were correlated visually with all tumors on ex vivo scintigraphic images by comparison of tissue morphology and the distribution of radioactivity (FIG. 6A-C). FIG. 6A is a photographic image of an excised CT-26 tumor 50 and excised left and right lymph nodes FIG. 6B is a scintigraphic image of the excised tumor and lymph nodes of FIG. 6A, showing significant radioactivity 60 localized to the tumor and little or no radioactivity localized to the lymph nodes. FIG. 6C is a image produced by fusing of the digital photographic image of FIG. 6A and the digital scintigraphic image of FIG. 6B, showing the correlation of radioactivity and the tumor.

Although lymph nodes are morphologically visible in the photographic image, little or no radioactivity was associated with them indicating a lack of tumor cell infiltration. The main tumor in FIG. 6 and FIG. 7 was histologically categorized as an adenocarcinoma. In other studies, a wide variety of subcutaneous tumors were scanned using microCT; all were easily detectable down to a size of less than 300 microns in diameter.

TABLE 1

Summary of Tumor Models

| Tumor Model | Species | Category | Uptake |
|---|---|---|---|
| Human Tumor Xenografts | | | |
| Prostate PC-3 | SCID Mouse | Adenocarcinoma | Yes |
| Lung A-549 (NSCLC) | SCID Mouse | Adenocarcinoma | Yes |
| Lung NCI H-69 (Oat Cell) | Nude Mouse | Adenocarcinoma | Yes |
| Adrenal H-295 | SCID Mouse | Adenocarcinoma | Yes |
| Adrenal RL-251 | SCID Mouse | Adenocarcinoma | Yes |
| Melanoma A-375 | Nude Mouse | Adenocarcinoma | Yes |
| Colon LS-180 | Nude Mouse | Adenocarcinoma | Yes |
| Ovarian HTB-77 | Nude Mouse | Adenocarcinoma | Yes |
| Animal Tumor Xenografts | | | |
| Mammary MCF-7 | Rat | Adenocarcinoma | Yes |
| Prostate MatLyLu | Rat | Adenocarcinoma | Yes |
| Walker-256 | Rat | Carcinosarcoma | Yes |
| Recent Rodent Models | | | |
| TRAMP prostate | Spontaneous mouse | Adenocarcinoma | Yes |
| Liver CT-26 | Mouse xenograft | Colorectal adenocarcinoma | Yes |
| Subcutaneous CT-26 | Mouse xenograft | Colorectal adenocarcinoma | Yes |
| Min Mouse Intestinal | Endogenous Mouse | Adenocarcinoma | Yes |
| Melanoma | Mouse xenograft | Adenocarcinoma | Yes |
| SCC1 and 6 | Nude mouse | Squamous cell carcinoma | Yes |
| Mammary SCC and ACC | $Apc^{Min/+}$mouse | Squamous cell carcinoma and Adenocarcinoma | Yes |
| Hepatocellular Carcinoma | Spontaneous TGF-α mouse | Adenocarcinoma | Yes |
| Pancreatic c-myc and kras | Spontaneous mice | Adenocarcinoma | Yes |
| Glioma L9 | Rat | Glioma | Yes |
| Retinoblastoma | Spontaneous Mouse | Blastoma | Yes |
| Cervical | Spontaneous Mouse | Adenocarcinoma | Yes |
| Adenomatous Polyp | Spontaneous Mouse | Adenoma | No |
| Mammary Hyperplasia | Endogenous Mouse | Alveolar Hyperplasia | No |

Since the tumor-targeting mechanism appears to involve selective tumor retention over time, relatively short-lived nuclides such as $^{18}$F or even $^{99m}$Tc are not practical for labeling at the current time. However, as with the early use of monoclonal antibodies, which were labeled exclusively with radioisotopes of iodine, it is possible to label PLE analogs with alternative labels, such as iodine-124, wherein the physical half-life matches well with PLE tumor uptake and retention kinetics. In addition to capitalizing on the resolution enhancement and 3-dimensional capabilities PET imaging affords relative to traditional gamma camera imaging, this approach would compliment the use of $^{18}$FDG in that its uptake into tumor cells occurs via a different biochemical mechanism than glucose utilization.

As has been discussed above, the utility of currently available tracers (e.g. $^{67}$Ga and $^{18}$FDG) is limited by lack of specificity to distinguish neoplasm from inflammation. However, preliminary studies with PLE agents has offered promise in overcoming this clinically significant limitation wherein carrageenan-induced granulomas in rats failed to visualize above background activity and showed no tissue retention. Counsell R E, et al. Tumor visualization with a radioiodinated phospholipid ether. J Nucl Med 31(3):332-336, 1990. Gallium citrate, however, utilized as a control in that study, did concentrate significantly in the granuloma. Such findings further justify extending the inventors' studies with PLE analog agents as potentially useful tumor-selective imaging agents.

Human Studies: Based upon the very promising pharmacokinetic and imaging data in animals, the inventors were encouraged to move studies of radiolabeled phospholipid ethers into the clinical arena. Unlabeled NM324 was initially assessed for its acute toxic effects on rats and rabbits in studies conducted at the Toxicology Research Center, State University of New (SUNY) at Buffalo. No toxic effects were seen at a dose level of 3.2 mg/kg (>150 times the highest anticipated human dose) in these acute dose toxicology studies. Moreover, no platelet activating properties were demonstrated at this high dose level.

Unlabeled NM324 was administered to five normal, disease-free, humans in order to gain approval of the radiolabeled agent for human administration by the Radioactive Drug Research Committee (RDRC). These subjects had no evidence of toxicity, as manifested by symptoms, clinical examination, vital signs and sequential blood chemistries.

As a pilot feasibility project, four lung cancer patients were studied under RDRC approval with $^{131}$I-labeled NM324 at the Ann Arbor, Mich. VA hospital. Lung tumors were clearly visualized in all three of the patients with lung cancer (two with NSCLC and one with small cell lung cancer), described in detail below. The degree of tumor uptake, at various time points, varied from 1+ (barely perceptible above background) to 3+ (intense uptake, much greater than normal structures). Note that the patients selected for these initial studies were those with known, relatively large cancers. It was not intended at this stage to study patients in whom problems of tumor staging existed.

Case Histories:

Patient 01 was a 55 year old woman with a right middle lobe lung mass eroding into the right ribs, histologically a mucin-producing adenocarcinoma of probable lung origin. Initial $^{131}$I-NM324 scintigraphic images at 6 hours showed a focus of uptake in the right lateral mid-lung. For reasons unrelated to the scintigraphic study, the patient was unable to return to the hospital beyond 6 hours for further imaging sessions.

Patient 02 was a 62 year old man with a large (9×7×7.5 cm), lobulated mediastinal mass extending from the aortopulmonary window and left hilum. Tissue type was a small cell undifferentiated (oat cell) carcinoma. $^{131}$I-NM324 scintigraphic images revealed a focus of uptake in the left upper lung, which increased in intensity over time relative to the normal background activity.

Patient 03, a 74 year old man with a right upper lobe NSCLC (adenocarcinoma) treated 5 months previously with radiation therapy. Disease recurred in the left lingula (2.5× 2×3 cm mass), lower thoracic spine (approx. T8) and right lobe of the liver. $^{131}$I-NM324 scintigraphy showed well defined uptake in the lung mass and thoracic spine lesion, which demonstrated increasing target to background ratios over time (FIG. 2). Uptake in the liver metastasis could not be resolved above the normal liver background.

These studies provided an early glimpse of the clinical promise of radiolabeled PLE analogs. Although $^{131}$I is a suboptimal isotope for imaging purposes, uptake in all three lung tumors was clearly depicted. As expected, based upon prior animal biodistribution experiments, activity in the tumors increased over time, as clearly demonstrated in patients 02 and 03. In patient 03 tumor-to-normal tissue ratios increased from 2.74 at 2 days to 4.23 at 7 days. Patient 01 did not return for later imaging sessions beyond 6 hours. The increasing target-to-background ratios constitute strong evidence that the mechanism for tumor visualization is not one based merely upon abnormal blood flow or tumor hypervascularity. Indeed, animal studies using $^{99m}$Tc human serum albumin confirmed this.

CT-26 Colon Adenocarcinoma Xenograft Model: NM404 was also evaluated in a xenograft colon adenocarcinoma tumor model whereby CT-26 cells (5×10$^5$ cells/50 µl) were previously injected directly into the liver parenchyma of female Balb/C mice for creation of focal liver tumors.

Imaging Studies: (FIG. 3A, 100 µg) was radioiodinated with $^{125}$I via isotope exchange in a melt of pivalic acid. Weichert J P, et al., Int J Applied Radiat Isot (1986) 37(8): 907-913. Following HPLC purification it was dissolved in an aqueous 2% Tween-20 solution prior to tail vein injection (high specific activity 15 µCi/20 g mouse) into 3 TGF-α endogenous mice or alternatively into 3 CT-26-tumor bearing mice. Mice were anesthetized and scanned for up to 21 days post injection on a modified Bioscan AR2000 radio-TLC scanner (2 mm increments at 2 min acquisition/lane and 1 mm high-resolution collimator) and also in an ImTek microCT scanner (390 steps) for anatomic correlation. MicroCT images were displayed using Amira software. At sacrifice, tumor-bearing livers were initially excised and scanned ex vivo. Tumors were then excised, weighed, scanned ex vivo, and radioactivity quantitated. Lesion samples were submitted for histologic classification.

Figures 9A, 9B:
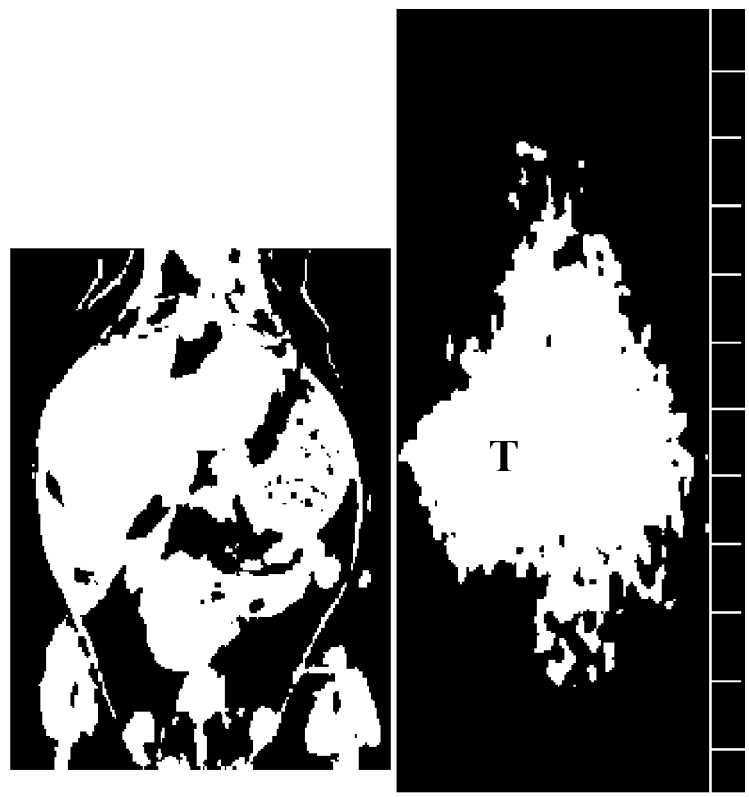
FIG. 9 shows the image of a coronal microCT scan (FIG. 9A) and dorsal scintographic image (FIG. 9B) of a TGF-α hepatoma-bearing mouse 10 days post $^{125}I$-NM404 injection. The liver is enhanced on microCT image using ITG, a hepatocyte-selective CT contrast agent (Tumor=T).
Figures 10A, 10B, 10C:
FIG. 10 shows a photograph image (FIG. 10A) and scintigraphic image (FIG. 10B) of the excised liver of a CT-26 tumor-bearing mouse seven days after a NM404 injection. Liver tumor involvement was extensive. Tumor implant occurred 15 days prior to this scan. Also shown are a scintographic image (FIG. 10C) and photographic image (FIG. 10D) of excised dissected tumors (T) and normal uninvolved liver (L).
Figures 11A, 11B, 11C:
FIGS. 11A-C presents microCT images of the same mouse presented in FIG. 10A-D, showing the presence of multiple CT26 tumors. Liver was enhanced using ITG, a hepatocyte-selective contrast agent. These images were acquired 10 days post tumor cell implantation and 5 days prior to the scintigraphic images of FIG. 10B and FIG. 10C. Tumors are indicated by arrows and the gall bladder by "GB".

Results and Discussions: Initial imaging results with NM404 (FIG. 9, FIG. 10) have shown striking uptake (>20% dose/g) and prolonged retention in both spontaneous and implanted carcinomas in the liver. Tumor retention of NM404 persisted in these animals for 21 days, the predetermined study endpoint. Contrast-enhanced microCT images confirmed the presence and precise location of all liver tumors (FIG. 9, FIG. 11). Lipid extraction and subsequent HPLC analysis of tumor tissue indicated that the radioactivity was still associated with parent compound. As has been observed in previous cell culture and in vivo animal model studies, NM404 apparently is metabolized and eliminated from normal cells, but becomes metabolically trapped in tumor cell membranes Conclusions: As has been the case in all prior tumor models examined, NM404 displayed selective and prolonged retention by both spontaneous and xenograft murine liver tumor models evaluated in this study.

Example 4

Specificity for Hyperplasia Versus Neoplasia in the Apc$^{Min/+}$ Endogenous Mammary Adenocarcinoma Model Materials and Methods: Apc$^{Min/+}$ Mouse Model: This model is comprised of mice carrying the Min allele of Apc (Apc$^{Min/+}$ mice). This model offers specific advantages over xenograft models in that female Apc$^{Min/+}$ mice are predisposed to develop mammary hyperplasias and carcinomas and intestinal adenomas. On the C57BL6/J genetic background, about 5% of untreated females will develop a mammary tumor by 100 days of age. Moser, A. R., et al. *Proc Natl Acad Sci USA* (1993) 90:8977-81. The incidence and multiplicity of the mammary lesions can be increased by a single dose of ethylnitrosourea (ENU), a direct acting alkylating agent. Treatment with ENU results in 90% of B6 Apc$^{Min/+}$ females developing an average of 3 mammary squamous cell carcinomas (SCC), but few hyperplasic lesions within 60 days after treatment.

Genetic background can affect the incidence, latency, and type of mammary lesions that develop. For example, FVBxB6 Apc$^{Min/+}$ female mice develop an average of 0.2 mammary tumors per mouse, but 4 hyperplasias per mouse within 120 days of treatment. Balb/xB6 Apc$^{Min/+}$ develop an average of 1.8 mammary tumors and 0.6 hyperplasias per mouse. Moser A R, Hegge L F, Cardiff R D. Cancer Research (2001) 61:3480-3485. FVBxB6 and BALBxB6 Apc$^{Min/+}$ mice develop both mammary SCC and adenocarcinomas (AC).

Figure 14:
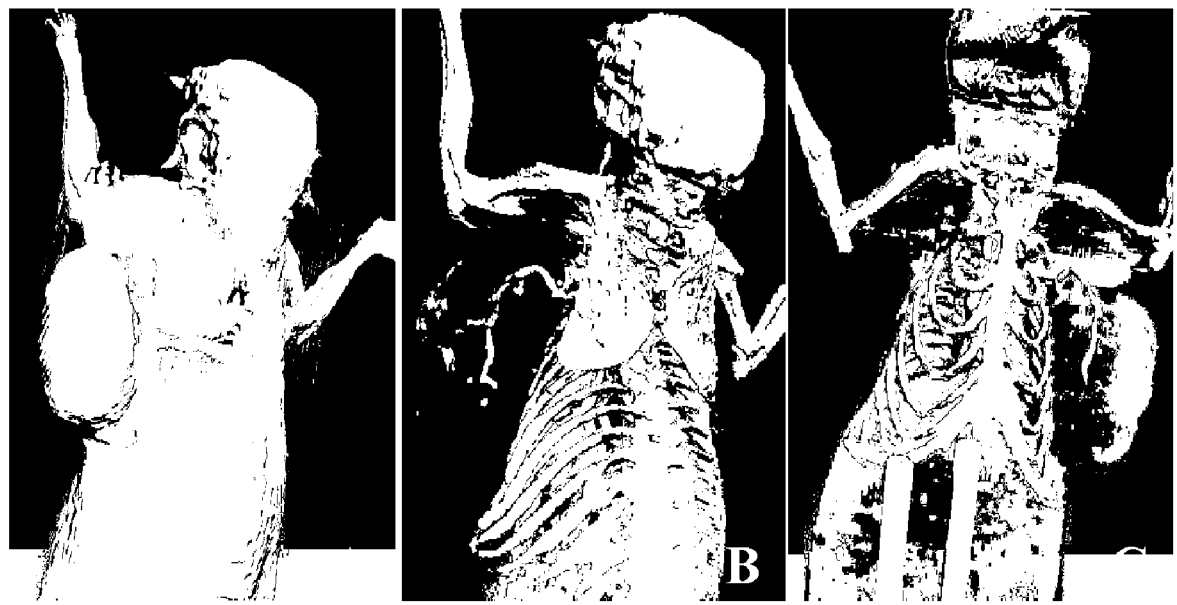
FIGS. 14A-C shows images of microCT scans of the Min mouse shown in FIG. 13A-E.

Imaging Studies: NM404 (FIG. 3A, 100 µg) was radioiodinated with $^{125}$I via isotope exchange in a melt of pivalic acid. Following HPLC purification it was dissolved in an aqueous 2% Tween-20 solution prior to tail vein injection (15 µCi/20 g mouse) into 6 female Apc$^{Min/+}$ mice. Mice were anesthetized and scanned for up to 30 days post injection on a modified Bioscan AR2000 radio-TLC scanner (2 mm increments at 2 min acquisition/lane and 1 mm high-resolution collimator) and also in an ImTek microCT scanner (390 steps) for anatomic comparison. MicroCT images were displayed using Amira software. At sacrifice, mammary glands or excised tumors were imaged ex vivo, lesions were excised, weighed, and radioactivity quantitated. Lesion samples were submitted for histologic classification. If necessary a long-acting CT blood pool contrast agent (BP20), developed in the inventors lab and suitable for long microCT acquisition times was injected intravenously prior to CT scanning in order to assist in blood vessel visualization (FIG. 14). Weichert J P, et al., Radiology (2000) 216:865-871.

Figures 12A, 12B, 12C, 12D:
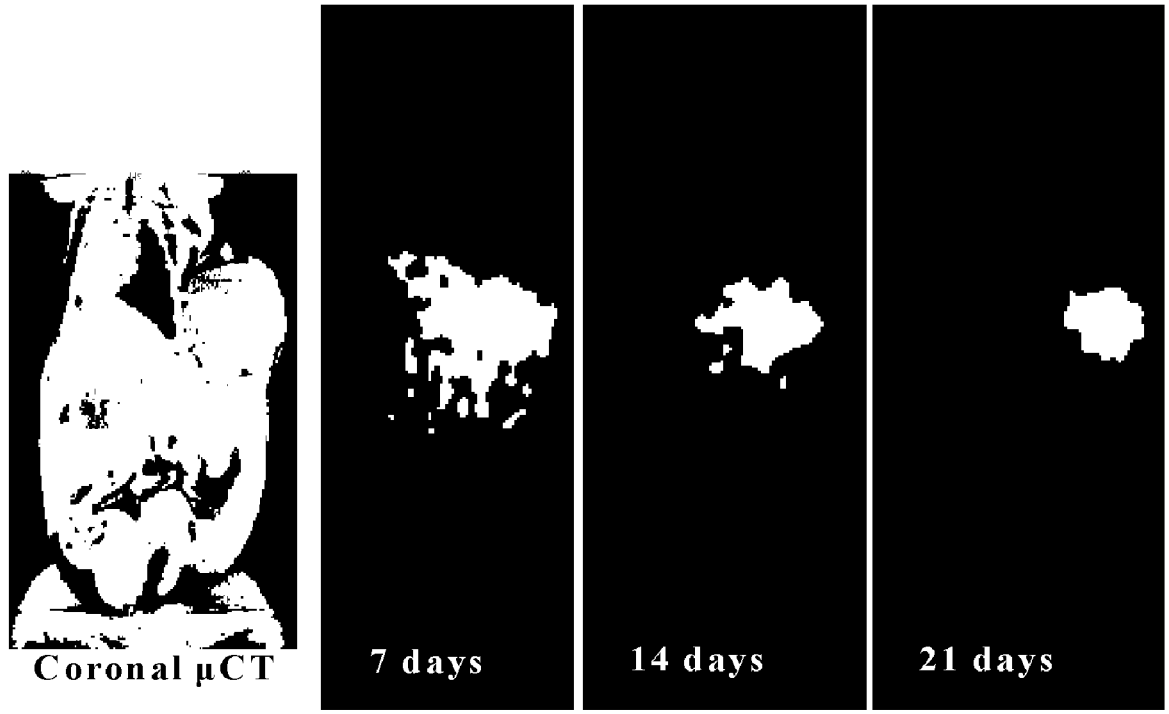
FIG. 12A-12D present scintographic images of a Min mouse with spontaneous right axillary mammary adenocarcinoma (10 mm dia) at various times following IV administration of $^{125}I$-NM404 (15 μCi).
Figure 13:
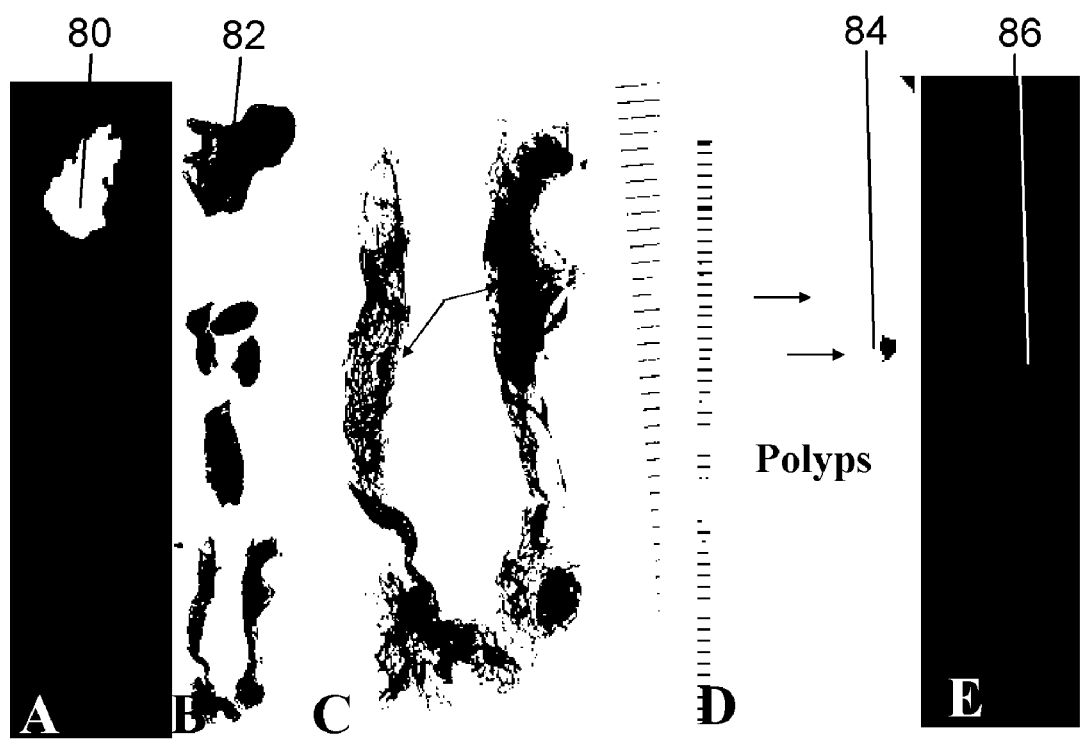
FIG. 13A and FIG. 13E are scintigraphic images of excised mammary glands and colon, respectively, from an FVBx B6Min mouse 8 days after administration of NM404. Corresponding photographic images of same excised mammary and colon tissues are in FIG. 13B and FIG. 13D, respectively. An enlarged photographic image of carmine-stained tissue (FIG. 13C) shows the presence of hyperplasias (arrows) but no corresponding focal radioactivity is seen in the scintigraphic image (FIG. 13A). The bright region 80 on the scintigraphic image (FIG. 13A) corresponds to larger adenocarcinoma 82 in FIG. 13B. A comparison of the photographic image (FIG. 13D) and scintigraphic image (FIG. 13E) of the excised colon indicates no uptake of NM404 in adenomatous polyps (cf. 84 and 86).

Results and Discussion: This model is unique in that hyperplastic mammary lesions, mammary carcinomas, and intestinal adenomas develop in the same mouse. Initial imaging results with NM404 (FIG. 12, FIG. 13) have shown striking uptake (>20% dose/g) and prolonged retention in all spontaneous mammary carcinomas ranging from 2-15 mm in diameter. Although tumor localization appears rapid, background radioactivity persists for several days in liver and gut during the body clearance phase. HPLC analysis of radioactive urine and feces indicated the presence of metabolites and no parent NM404. Tumor retention of NM404 persisted for >21 days, the predetermined study endpoint. NM404 did not localize, however, in either focal alveolar hyperplasias or in intestinal adenomatous polyps found frequently in these mice (FIG. 13). MicroCT images confirmed the presence and precise location of all mammary tumors (FIG. 14). NM404 apparently is metabolized and eliminated from normal cells but becomes metabolically trapped in tumor cell membranes.

Conclusions: NM404 has displayed striking tumor avidity in 25/25 animal and human xenograft tumor models examined to date. Moreover, while it displayed selective and prolonged retention by mammary adeno- and squamous cell carcinomas in this spontaneous tumor model, it did not localize in associated focal alveolar hyperplasias or intestinal adenomatous polyps and thus appears to be selective for malignant tumor cells.

Example 5

Mechanism of Selective Retention of NM404

Introduction: Certain phospholipid ether analogs, such as NM404, are selectively retained within many types of tumor cells for a prolonged time. The inventors sought to evaluate the mechanism of selective retention of NM404 in tumor cells using both an enzymatic assay to evaluate the activity of phospholipase D (PLD) protein by assay and PLD expression by quantitative PCR. The inventors hypothesized that reduced levels of PLD in tumor cells results in a decrease in the ability to metabolize and excrete NM404.

Methods: Single cell suspensions of murine tumor cell lines including hepa-1 (hepatoma), CT26 (colorectal adenocarcinoma), and TS/A (breast adenocarcinoma) were analyzed with two assays: (1) Amplex® Red assay, using a commercially available kit (Molecular Probes) that evaluates PLD activity using a fluorescence microplate reader, and (2) quantitative PCR to determine the level of PLD mRNA. Tumor cell lines were compared to normal tissue. For the Amplex® Red assay, total protein was extracted using a detergent solution (Triton-X-100) and quantity of PLD compared to a standard positive control. For PCR, mRNA was purified and converted to cDNA using reverse transcriptase (Promega). Conditions for amplification of cDNA for real-time PCR included: (94° C., 30 sec; 65° C., 30 sec; and 72° C., 30 sec) for 50 cycles (iCycler, iQmix, Bio-Rad). The primer pair for PLD1, (sense) 5'-TCTGGTTTCACCCCGTCAGAA-3' (SEQ ID NO: 1), (antisense) 5'-TTGCTCATATCTGCGGCGAT-3' (SEQ ID NO:2), were used. Product was compared to a standard cDNA (GAPDH, Biosource) diluted from 1 µg to $10^{-7}$ µg. All assays were performed in duplicate.

Results: PLD was quantified as shown in Table 2, below. Both PLD protein activity and mRNA levels were significantly lower than normal liver tissue (p<0.05, T-test) in all tested cell lines.

TABLE 2

| Cell/tissue | PLD protein activity (mU/fluorescence/µg protein/ml) | mRNA (µg × $10^{-5}$/ 0.01 µg of total cDNA) |
|---|---|---|
| Hepa-1 | 3.3 | 6.2 |
| CT26 | 7.8 | 2.4 |
| TS/A | 2.8 | 4.0 |
| Normal liver | 14.1 | 12.2 |

Conclusion: Both reduced PLD protein activity and a decrease in PLD expression as mRNA were observed in murine tumor cell lines. Thus, the mechanism of selective retention of NM404 may be due to the apparent lack of metabolic phospholipase enzyme present in malignant tumor cells causing the agent to become biochemically locked into these cells. Decreased PLD activity in tumor cells and malignant tissue can also serve as a molecular target for other candidate anti-tumor agents.

Example 6

Therapeutic Effects of NM404 in an Endogenous Murine Mammary Tumor Model

Figure 16:
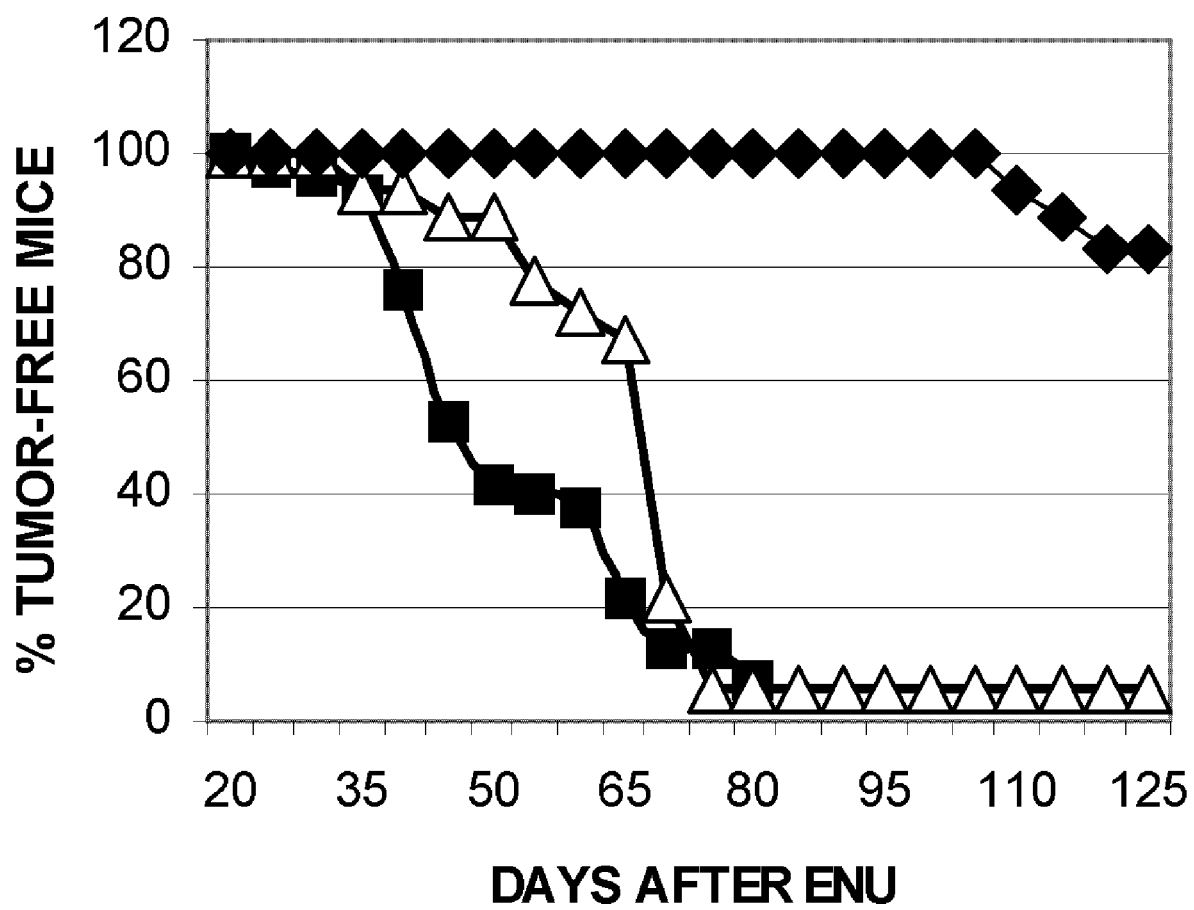
FIG. 16 is a graphical representation of time to first tumor after ENU-treated in different strains of Min/+mice. Time to first mammary tumor expressed as days after ENU. Female Min/+mice were treated with ENU and checked twice weekly for the presence of mammary tumors. The time after ENU treatment to first tumor is plotted in 5 day intervals for B6Min/+(n=45)(□), BRB6 Min/+(n=18)(Δ), FVBB6 Min/+ (n=18) (◇).

Models for NM404 Therapy Study: Although long-term survival is not essential for imaging studies, it is advantageous for the proposed therapy studies. The models used for imaging studies suffer from concomitant intestinal tumors which usually lead to the death of the animal. In order to increase the number of tumors developing per mouse and decrease the number of intestinal tumors in hopes of increasing the lifespan of the tumor bearing mice, male B6 Min/+ mice were crossed with female C57BR/cdJ (BR) mice. The resulting BRB6 F1 Min/+ female mice developed significantly more mammary tumors after ENU treatment than did the B6 Min/+ mice (P=0.016), an average of nearly 5 per mouse. The number of mice with tumors and the time to first tumor were not different between these two strains (P=1 and P=0.06, respectively) (FIG. 16). The increased mammary tumor number of the BRB6 F1 mice may be due, in part, to the significantly longer survival times of the hybrid BRB6 F1 Min/+ mice relative to the B6 Min/+mice (P=$2 \times 10^{-7}$).

B6 and BRB6 F1 Min/+ mice were very similar with respect to the mammary gland phenotype, but quite different in susceptibility to intestinal tumors. The B6 and BR strains can be considered sensitive backgrounds for Min-induced mammary tumorigenesis as the mice developed a large number of tumors within a short time after ENU treatment. However, the BR strain carries dominant resistance alleles at modifier loci affecting intestinal tumor development, which may prove relevant to further therapeutic considerations.

Imaging Results with NM404 in Min Mice: In a study to show that NM404 localizes in endogenous FVBxB6 Apc$^{Min/+}$ mouse breast tumors, two animals were injected (IV tail vein) with $^{125}$I-NM404 (15 µCi) and imaged on a modified Bioscan AR2000 radioTLC scanner (equipped with high resolution 2 mm collimator and 2-D acquisition and analysis software) at 1, 4, and 7 days post injection (FIG. 17A, FIG. 17B). Each animal underwent microCT scanning (FIG. 17) on day 10 prior to euthanasia and dissection to remove the mammary glands and associated tumors. Focal hot spots correlated visually with all tumors on ex vivo scintigraphic images (FIG. 17C). Although lymph nodes are visible, no radioactivity was associated with them, indicating a lack of tumor cell infiltration. The main tumor in FIG. 17C was histologically categorized as an adenocarcinoma. There were four mammary tumors in both mice and all were easily detectable in ex vivo scintigraphic images of the excised mammary glands.

Radiotherapeutic Effects of NM404: During the course of recent mouse tumor uptake and retention studies with "imaging" doses (15-20 µCi/20 g mouse) of $^{125}$I-labeled NM404, several apparent therapeutic responses have been observed. In an Apc$^{Min/+}$ mouse mammary tumor model, it has generally been noted that tumor growth remains static following a single intravenous injection of NM404. Some of these animals also lost all hair above larger mammary tumors at around 8 days after injection. Moreover, these mice also get intestinal tumors and usually suffer from intestinal bleeding resulting in severe anemia, which renders their feet white. It was noted that the feet of these mice had reverted to a pink color around 5 days after a single injection of NM404. Dissection of these animals revealed very few, if any, of the expected 20 or so intestinal tumors per mouse usually found at this age.

The "white to pink feet" phenomenon was also observed in a separate, but more aggressive, mouse intestinal adenocarcinoma model, wherein dissection at 12 days following NM404 administration, again revealed that very few, if any, of the expected intestinal tumors were present. In both intestinal tumor models, animals that received NM404 easily outlived their untreated litter mates. These findings were reconfirmed in two separate age-matched groups each involving more than 6 mice. These observations with $^{125}$I-NM404 indicate the potential of this compound as well as $^{131}$I-NM404 as an agent for radiotherapy applications.

Figure 18:
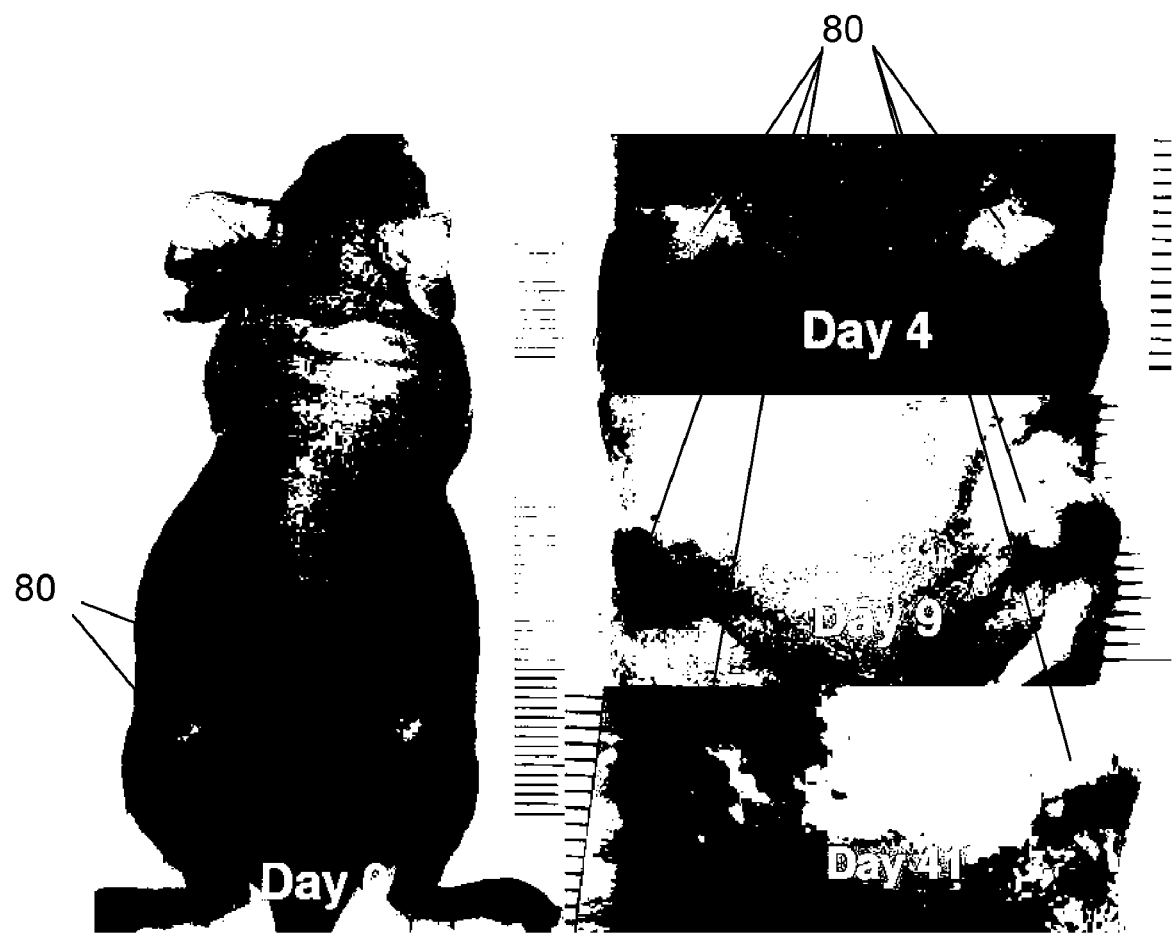
FIG. 18 is a set of photographs of the back of a mouse showing SCC1 and SCC6 tumors 80 in a time series at days 0, 4, 9 and 41 after an injection of $^{125}$I-NM404 illustrating a reduction in size of the tumors 80.

Choice of Isotope: Due to its 60-day physical half-life and low energy 35 KeV photon emission, $^{125}$I is suitable for imaging experiments in mice and rats. $^{125}$I also affords therapeutic characteristics as well and is currently used in permanent prostate brachytherapy implants. In one imaging study, 2 nude mice were each inoculated with subcutaneous squamous cell 1 and 6 tumor cell implants on opposing flanks. SCC 1 and SCC 6 cells were used because one is radiosensitive relative to the other. After 14 days when the average tumor size (4 total) was approaching 0.5 cm in diameter, one of the mice received 20 μCi of $^{125}$I labeled NM404 and the other one receive unlabeled NM404 in an equal mass dose. The mouse that had received only the unlabeled compound had to be euthanized 20 days after injection due to both tumors reaching the termination size limit as defined in our animal use protocol. Both tumors in the $^{125}$I-NM404 mouse regressed dramatically over the course of several weeks (FIG. 18). In fact, the tumors of this mouse never did reach terminal size and the mouse was actually euthanized after 80 days in order to collect histology sections. At this time, the center of the tumor had become necrotic while the peripheral rim appeared somewhat viable. Histologic examination confirmed a necrotic center and viable rim. While blood supply factors can contribute to such observations it is also possible that the photon emission from $^{125}$I resulted in poor electron equilibrium at the tumor periphery resulting in under-dosing of the "rind" of the tumor. This electron equilibrium issue is critical in radiation oncology. Photons travel a finite distance, determined by their energy, before interacting with tissue and exerting their biologic effect. A photon with too high an energy can result in under-dosing of the tumor nodule periphery, as photons departing the nodule travel away (out of the tumor) before depositing their dose. However, with $^{125}$I, the photons have relatively low energy, insuring very local deposition. While complex Monte Carlo calculations could refine such estimates, but the best method for determining optimal isotope selection is experimentation, as there are many factors at play which cannot be modeled accurately (details of tissue distribution, multiple pass, etc). The one advantage of $^{125}$I is that all the photons are of low energy, insuring very limited exposure of normal tissues surrounding the tumor.

$^{131}$I has been used with great efficacy in the treatment of thyroid cancer. Very safe doses of $^{131}$I can control subclinical deposits of well-differentiated thyroid cancer, which concentrates iodine very avidly as does the normal thyroid. This active uptake process helps limit the dose to normal tissues. Iodine-131 has both beta and several gamma emissions, but the predominant tissue dose arises from the beta emissions. The inventors have selected $^{131}$I labeled NM404 based upon the clinical success with thyroid cancer coupled with results obtained with Bexxar (an $^{131}$I-labeled antibody-based agent) in low-grade lymphoma patients. The predominant beta emissions and mostly low energy gamma emissions optimize dose homogeneity within the tumor nodule itself Also, the shorter half-life (8-days) provides more clinically relevant dose-intensity compared to the 60-day half-life of $^{125}$I. These factors will permit the inventors to make the best assessment of the efficacy of this agent. A potential disadvantage of $^{131}$I is that there is a higher energy gamma emission as well which could actually expose adjacent surrounding tissues to more radiation than would occur with $^{125}$I. The tumors in the endogenous model proposed herein are peripherally located in the mammary glands and thus should not represent an immediate threat to the overall well-being of the animal. Since organ toxicity is also one of the study endpoints, the reaction of the surrounding tissue and key organ systems (marrow, liver, kidneys, bowel, brain, etc) is assessed. Tissue distribution data and actual dosimetry of radiolabeled NM404 will determine its optimal therapeutic potential. It is possible that different isotopes will complement each other in the therapeutic setting.

Example 7

Dual Modality Virtual Colonoscopy Using NM404 Composition

Dual Modality PET/CT Virtual Colonoscopy: Virtual colonoscopy, a non-invasive scanning procedure performed by CT scanning in humans has been reported to be more accurate than traditional colonoscopy. (Pickhardt P J. et al., Computed tomographic virtual colonoscopy to screen for colorectal neoplasia in asymptomatic adults. *New England Journal of Medicine.* 349(23):2191-200, 2003 Dec. 4. Performed on a traditional multidetector helical CT scanner, virtual colonoscopy allows one to noninvasively scan the intestinal lumen anatomically for tumors but cannot characterize space occupying lesions as either polyps (adenomas) or adenocarcinomas (malignant). Determination of tumor type dramatically effects treatment planning and outcome for these patients.

Using the method of the present invention, by pre-administering a tumor selective positron emitting agent (like $^{18}$F-FDG or $^{124}$I-NM404) and scanning the subject on a hybrid CT/PET scanner, a skilled artisan can both anatomically detect (CT) and functionally classify (PET) malignant tumors less invasively than by using endoscopic methods such as colonoscopy. Since NM404 is known to be taken up and selectively retained for prolonged periods of time by malignant tumor cells and not hyperplastic precancerous cells (see FIG. 19-FIG. 24), malignant tumors would exhibit high amounts of radioactivity (glow) during the reconstructed virtual fly through of the intestinal lumen whereas adenomatous polyps would not light up on the PET component of the dual modality scan. Intestinal tumor types can thus be classified without resort to invasive methods such as endoscopy. As noted above, radiolabeled phospholipid ether analogs such as $^{124}$I-NM404 are selectively retained in malignant tumor cells and thus provide significant advantages over $^{18}$F-FDG which lacks tumor specificity and is known to be taken up by both inflammatory sites and areas of hyperplasia (Barrett's Esophagus) in addition to tumors.

The results have demonstrated that NM404 is selectively taken up and retained by malignant tumor cells in mouse models and have performed virtual colonoscopy in mice using a microCT scanner. NM404 is currently undergoing evaluation in human lung cancer patients and early results indicate it is taken up and selectively retained in this human cancer in a similar fashion exhibited previously in 25/25 animal tumor models. Moreover, due to its uptake and prolonged selective retention in tumors, the inventors have observed significant tumor regression due to its radiotherapeutic effects in several different mouse tumor models. Agents such as radiohalogen labeled NM404 can thus be characterized this as a "Diapeutic™" since it can both detect and treat malignant tumors. It follows then that simultaneous detection and characterization of intestinal malignancies with NM404 CT/PET scanning can also result in subsequent treatment of the subject with a therapeutic dose of a phospholipid ether analog such as NM404 labeled with a radiohalogen selected from $^{124}$I, $^{125}$I or $^{131}$I or mixtures thereof.

A NM404 composition formulated for intravenous injection was administered as described above. The methods used in this Example were essentially those described in Pickhardt, P. J., et al., Microcomputed tomography colonography for polyp detection in an in vivo mouse tumor model, Proc. Natl. Acad. USA, 2005, 102: 3419-3422. All animal studies were conducted under approved guidelines set forth by the Institutional Animal Care and Use Committee of the American Association for Assessment and Accreditation of Laboratory Animal Care at the University of Wisconsin. The congenic strain used for this study was created by introducing the Min allele of the Apc gene from the C57BL/6J genetic background onto the C57BL/6J Tyr$^{c-2J}$/+ genetic background by back-crossing for 10 generations. This congenic strain developed an average of 2.1±0.4 (SEM) colonic tumors per mouse (range, 0-7) in 20 mice. This strain represents a good system for evaluation of microCT colonography because the number of colonic tumors is relatively high, compared with other mouse models of human colorectal cancer.

A total of 20 congenic mice were selected for microCT scanning. The mice were provided a diet of fresh vegetables, raw unsalted sunflower nuts, and water for 2 days ad libitum, followed by cherry-flavored NuLYTELY (Braintree Scientific) for 16 h before microCT scanning. This dietary approach significantly decreases the streak artifacts in microCT created by bone meal and other high-density fillers that are often found in normal pelleted mouse chow. The 20 mice (17-22 g body weight) were anesthetized with pentobarbital (0.06 mg/g body weight, i.p. injection), given an enema consisting of 1-1.5 ml of corn oil, and scanned for colonic tumors using microCT. The intestinal tract was filled retrogradely with heavy barium (225 wt/vol %) prior to MRI and CT scanning.

Anesthetized mice were scanned in the prone position immediately after rectal administration of contrast material. Images were acquired on a microCT scanner (Micro-CAT I, ImTek, Knoxville, Tenn.) by using the following imaging parameters: 43-kV peaks, 410 µA, 390 steps, 20-min scan duration. No i.v. contrast was administered, nor was an attempt made to gate image acquisition for peristaltic or respiratory motion, given the long acquisition times involved. Image data were reconstructed as 256×256×256 voxels (200-µm spatial resolution) by using a Shepp-Logan filter with back projection and no beam-hardening correction over an appropriate subvolume. Although much higher resolution is possible with these scanners, in practice, these acquisition and reconstruction parameters easily afford more than adequate spatial resolution while minimizing the radiation dose to the live subject. Anesthetized mice were euthanized immediately after CT scanning.

The microCT image data from each mouse were analyzed by using commercially available visualization software (AMIRA, Version 3.1, TGS, San Diego), which displayed the data as 2D axial, sagittal, and coronal cross-sectional images. The lumen of the colon near the rectum was marked by the end of the syringe, which prevented the contrast agent from flowing out during the scan. The radiologists were able to follow the colonic lumen from the rectum to the cecum. Window-level settings for the 2D displays were optimized for polyp detection, similar to that used for CT colonography in humans. The relative location and size of each detected lesion was marked on a schematic map of the mouse colon to facilitate matching the radiologic information with retrospective gross pathologic findings on necropsy. The excised colon was dissected and photographed to corroborate the morphological presence and location of colon tumors.

Gross pathologic inspection of the excised mouse colon served as the gold standard against which the microCT results were compared. Mice were killed immediately after the microCT scan. The colon was removed, opened longitudinally, digitally photographed, washed with PBS, and photographed again. A total of 41 colonic tumors and 33 fecal pellets were identified. The tumors ranged in size from ~1 mm to up to 5 mm. This procedure provided the ability to co-register tumors and fecal pellets observed during necropsy to those identified and mapped by using in vivo microCT images.

Figure 19A:
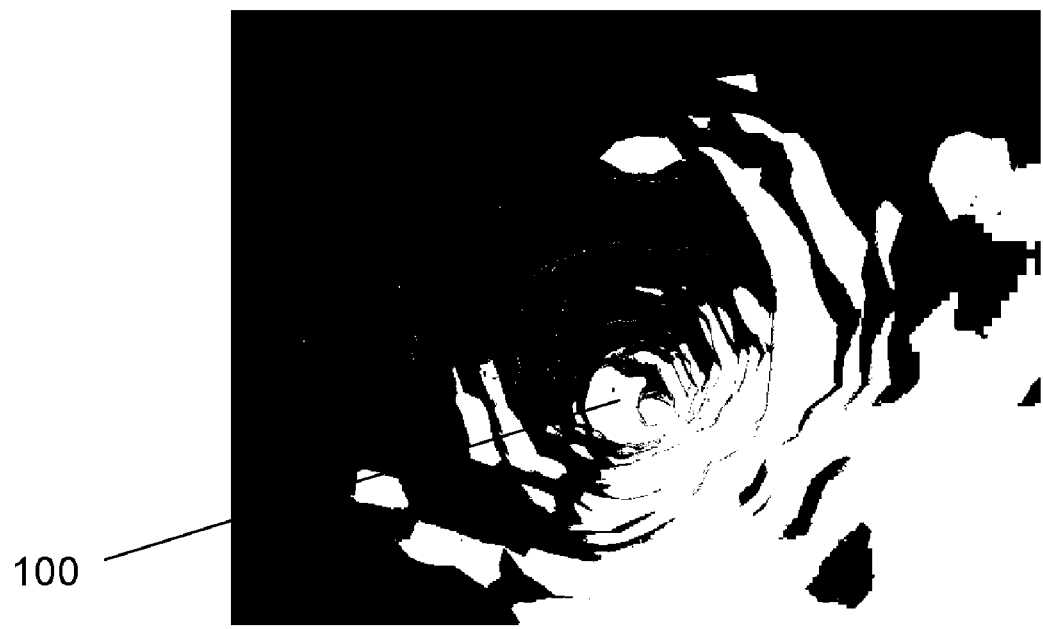
FIG. 19A and FIG. 19B are images of microCT surface-rendered scans of an excised mouse colon, showing in FIG. 19A, a tumor 100 that protrudes into the lumen of the colon from a distance, and in FIG. 19B, the tumor 100 from a closer vantage point.
Figure 19B:
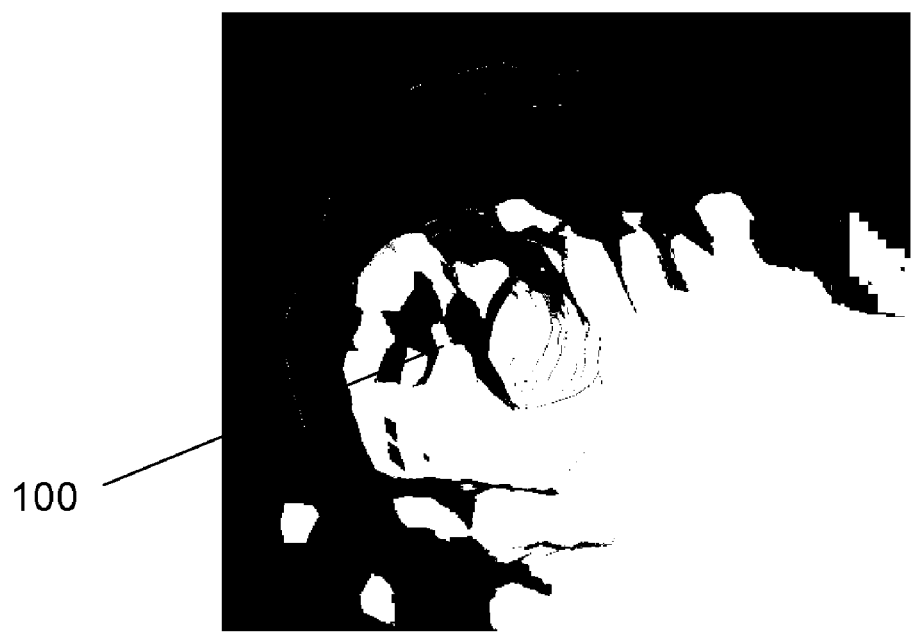

FIG. 19A and FIG. 19B are images of microCT surface-rendered scans of an excised mouse colon, showing in FIG. 19A, a tumor 100 that protrudes into the lumen of the colon from a distance, and in FIG. 19B, the tumor 100 from a closer vantage point.

Figure 20A:
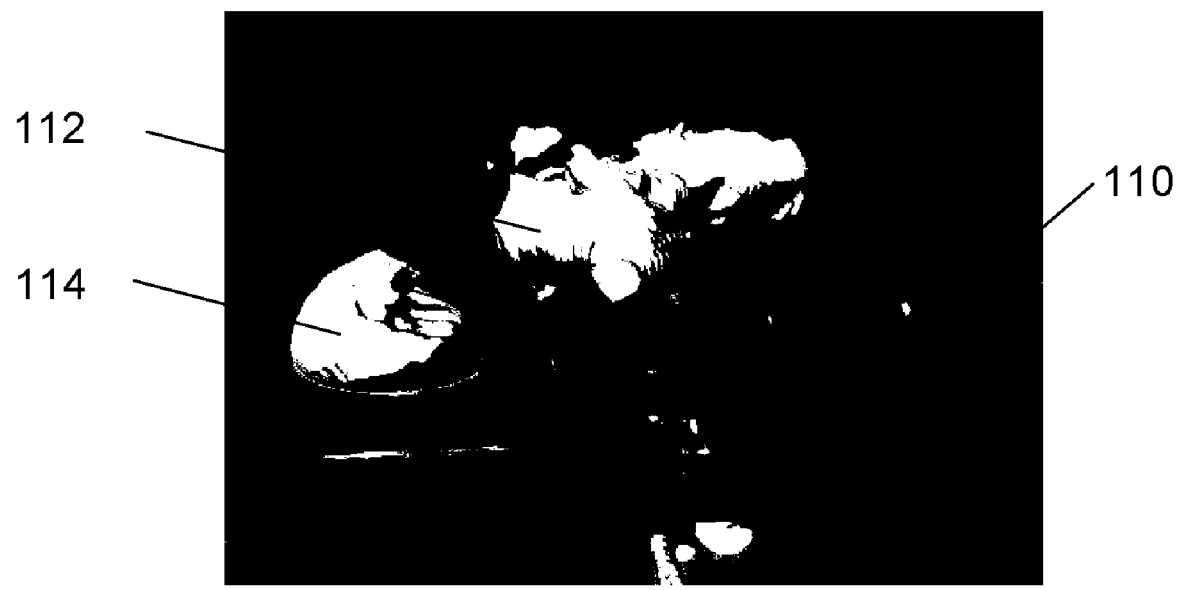
FIG. 20A and FIG. 20B are high-density surface rendered microCT images of the contrast-enhanced lower GI tract of an anesthetized mouse, with a planar coronal slice image 110 included to landmark the position of the colon 112 and cecum 114 of the lower bowel. The density of the barium-filled lower bowel actually exceeds that of neighboring bones 116 due to the high barium concentration in the lumen of the lower bowel; most soft tissue is excluded from view with the high density setting.
Figure 20B:

FIG. 20A and FIG. 20B are high-density surface rendered microCT images of the contrast-enhanced lower GI tract of an anesthetized mouse, with a planar coronal slice image 110 included to landmark the position of the colon 112 and cecum 114 of the lower bowel. The density of the barium-filled lower bowel actually exceeds that of neighboring bones 116 due to the high barium concentration in the lumen of the lower bowel; most soft tissue is excluded from view with the high density setting.

FIG. 21A and FIG. 21B are surface rendered (FIG. 21A) and transparent rendered (FIG. 21B) microCT images of the contrast-enhanced lower GI tract of an anesthetized mouse, showing the colon 112 and cecum 114 of the lower bowel. FIG. 21B also shows the distinction between a tumor 117 and a benign structure, a fecal pellet 119.

FIG. 22 is a photograph of an excised and dissected mouse colon 120 with a 3.5 mm diameter tumor 122.

Figures 23A, 23B:
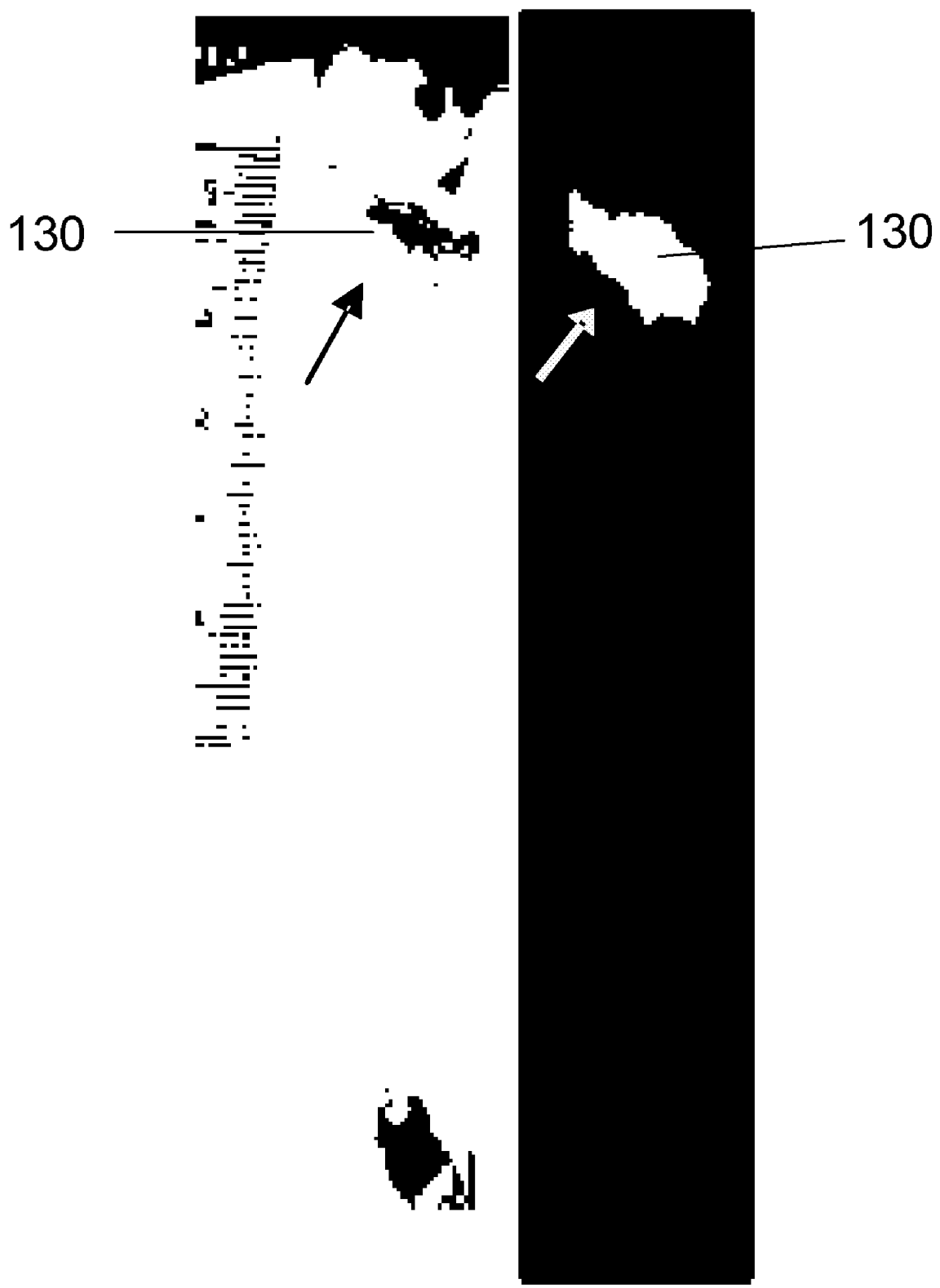
FIGS. 23A-B are photograph (FIG. 23A) and corresponding scintigraphic (FIG. 23B) images of an excised jejunum/ileum section of intestine. The Min mouse with intestinal adenocarcinomas was imaged 3 days post $^{125}$I-NM404 administration. Tumor 130 (arrow) measured 9×18 mm.
Figure 24A:
FIGS. 24A-E are scintographic images of excised Min Mouse duodenum (FIG. 2A, stomach juncture at top)), jejunum (FIG. 2B), jejunum/ileum (FIG. 2C), ileum (FIG. 2D), and colon (FIG. 2E), intense tumor uptake of radiolabelled NM404. All images are normalized for the same number of counts.
Figure 24B:
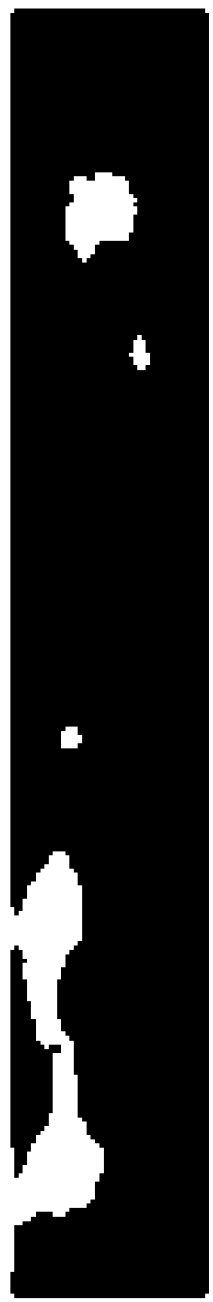
Figure 24C:
Figure 24D:
Figure 24E:

FIG. 23A-B are photograph (FIG. 23A) and corresponding scintigraphic (FIG. 23B) images of an excised jejunum/ileum section of intestine. The Min mouse with intestinal adenocarcinomas was imaged 3 days post $^{125}$I-NM404 administration. Tumor 130 (arrow) measured 9×18 mm.

FIGS. 24A-E are scintographic images of excised Min Mouse duodenum (FIG. 2A, stomach juncture at top)), jejunum (FIG. 2B), jejunum/ileum (FIG. 2C), ileum (FIG. 2D), and colon (FIG. 2E), intense tumor uptake of radiolabelled NM404. All images are normalized for the same number of counts. FIG. 2C is 10 cm long.

Figure 25A:
FIG. 25A shows a superposition of a 3D surface-rendered MRI image 400 and 3D microPET image 420 obtained 24 h after iv injection of $^{124}$I-NM404 (100 μCi) into a rat with a CNS-1 glioma brain tumor. Images were fused using Amira (v3.1) software (TGS, Inc., San Diego, Calif.).
Figures 25B, 25C:
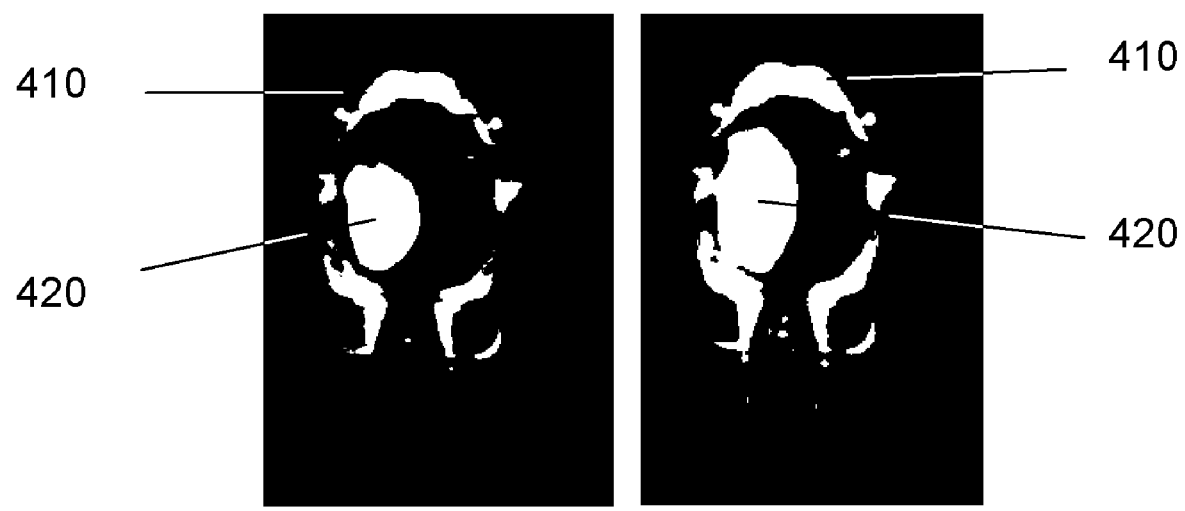
FIG. 25B is a contrast-enhanced coronal MRI slice 410 through the tumor 420 and FIG. 25C shows superimposed coronal MRI and $^{124}$I-NM404 microPET images corroborating the presence and location of the tumor.

Alternatively, other morphological techniques such as MRI can be used in conjunction with PET in place of CT scanning in the dual modality virtual colonoscopy of the present invention. FIG. 25A shows a superposition of a 3D surface-rendered MRI image 400 and 3D microPET image 420 obtained 24 h after iv injection of $^{124}$I-NM404 (100 µCi) into a rat with a CNS-1 glioma brain tumor. Images were fused using Amira (v3.1) software (TGS, Inc., San Diego, Calif.). FIG. 25B is a contrast-enhanced coronal MRI slice 410 through the tumor 420 and FIG. 25C shows superimposed coronal MRI and $^{124}$I-NM404 microPET images corroborating the presence and location of the tumor.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method of diagnosing cancer in a selected region of the intestinal tract using dual modality virtual colonoscopy in vivo, comprising the steps of:
   administering the radiolabeled 18-(4-iodophenyl)-octadecylphosphocholine;
   using computed tomography or magnetic resonance imaging to produce a visualization of the three-dimensional morphology of the selected region suspected of having a malignant tissue;
   using positron emission tomography or single photon emission tomography to produce a visualization of the distribution of the radioactivity produced by the radiolabeled 18-(4-iodophenyl)-octadecylphosphocholine; and
   comparing the visualization of the morphology of the selected region to the visualization of the distribution of the radioactivity produced by the radiolabeled 18-(4-iodophenyl)-octadecylphosphocholine, wherein the presence of radioactivity indicates the malignant tissue.

2. The method of claim 1 wherein the malignant tissue comprises adenocarcinoma cells.

3. The method of claim 1 wherein 18-(4-iodophenyl)-octadecylphosphocholine is radiolabeled with a halogen isotope selected from the group consisting of $^{123}$I, $^{124}$I, $^{131}$I, and mixtures thereof.

4. The method of claim 1 wherein the radiolabeled 18-(4-iodophenyl)-octadecylphosphocholine is a positron emitter.

5. The method of claim 3 wherein the radiolabeled 18-(4-iodophenyl)-octadecylphosphocholine is selected from the group consisting of $^{123}$I-18-(4-iodophenyl)-octadecylphosphocholine, $^{124}$I-18-(4-iodophenyl)-octadecylphosphocholine, $^{131}$I-18-(4-iodophenyl)-octadecylphosphocholine, and mixtures thereof.

6. The method of claim 1 wherein the selected region of the intestinal tract is the colon.

7. The method of claim 1 wherein the step of comparing the visualization of the morphology of the selected region to the visualization of the distribution of the radioactivity produced by the radiolabeled 18-(4-iodophenyl)-octadecylphosphocholine includes the step of producing an image of a three-dimensional structure by the reconstruction of two-dimensional images.

8. The method of claim 1 wherein the step of comparing the visualization of the morphology of the selected region to the visualization of the distribution of the radioactivity produced by the radiolabeled 18-(4-iodophenyl)-octadecylphosphocholine includes the step of superimposing the visualization of the distribution of the radioactivity produced by the radiolabeled 18-(4-iodophenyl)-octadecylphosphocholine on the visualization of the morphology of the selected region.

9. The method of claim 1, wherein the first technique is computed tomography and the second technique is positron emission tomography.

10. The method of claim 1, wherein said malignant tissue is colorectal cancer.

11. The method of claim 9, wherein said malignant tissue is colorectal cancer.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
tctggtttca ccccgtcaga a       21

<210> SEQ ID NO 2
<211> LENGTH: 20
<212> TYPE: DNA
<213> ORGANISM: Artificial
<220> FEATURE:
<223> OTHER INFORMATION: PCR Primer

<400> SEQUENCE: 2
ttgctcatat ctgcggcgat       20